(12) United States Patent
Kim

(10) Patent No.: US 10,295,975 B2
(45) Date of Patent: May 21, 2019

(54) PROCESSING BOARD, MEDICAL DIAGNOSTIC APPARATUS, AND METHOD OF CONTROLLING THE MEDICAL DIAGNOSTIC APPARATUS

(71) Applicant: SAMSUNG ELECTRONICS CO., LTD., Suwon-si (KR)

(72) Inventor: Myeong Je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 830 days.

(21) Appl. No.: 14/851,087

(22) Filed: Sep. 11, 2015

(65) Prior Publication Data
US 2016/0124406 A1 May 5, 2016

(30) Foreign Application Priority Data
Nov. 4, 2014 (KR) ........................ 10-2014-0152096

(51) Int. Cl.
*A61B 6/04* (2006.01)
*G05B 19/02* (2006.01)
(Continued)

(52) U.S. Cl.
CPC ............ *G05B 19/02* (2013.01); *A61B 6/4411* (2013.01); *A61B 6/4429* (2013.01); *A61B 6/4494* (2013.01); *A61B 6/586* (2013.01); *G05B 19/042* (2013.01); *A61B 5/055* (2013.01); *A61B 6/4464* (2013.01); *A61B 6/461* (2013.01); *A61B 6/547* (2013.01); *A61B 6/563* (2013.01); *A61B 8/4411* (2013.01); *A61B 8/4438* (2013.01); *A61B 8/54* (2013.01); *A61B 8/565* (2013.01);
(Continued)

(58) Field of Classification Search
None
See application file for complete search history.

(56) References Cited

U.S. PATENT DOCUMENTS 8,554,953 B1 * 10/2013 Sorensen ................. A61B 7/04
710/2
8,821,016 B2 * 9/2014 Yang .................... A61B 6/4233
378/205

(Continued)

FOREIGN PATENT DOCUMENTS

JP    2008000430 A    1/2008
JP    2011523869 A    8/2011
(Continued)

OTHER PUBLICATIONS

Communication dated Feb. 29, 2016, issued by the Korean Intellectual Property Office in counterpart Korean Application No. 10-2014-0152096.

*Primary Examiner* — Thomas R Artman
(74) *Attorney, Agent, or Firm* — Sughrue Mion, PLLC

(57) ABSTRACT

A processing board mounted on a medical diagnostic apparatus, the medical diagnostic apparatus, and a method of controlling the medical diagnostic apparatus are provided. The processing board includes a sensor configured to sense at least one selected from the group consisting of an installation position, an installation direction, and a power consumption of the processing board. The processing board further includes a controller configured to set an identifier (ID) of the processing board based on an output signal of the sensor.

23 Claims, 17 Drawing Sheets

(51) Int. Cl.
    *G05B 19/042*     (2006.01)
    *A61B 6/00*     (2006.01)
    *A61B 5/055*     (2006.01)
    *A61B 8/00*     (2006.01)

(52) U.S. Cl.
    CPC ......... *A61B 8/58* (2013.01); *A61B 2560/0462* (2013.01); *G05B 2219/25032* (2013.01); *G05B 2219/2652* (2013.01)

(56) References Cited

U.S. PATENT DOCUMENTS

| | | | |
|---|---|---|---|
| 9,872,320 B2* | 1/2018 | Jun | G16H 40/63 |
| 2009/0300507 A1* | 12/2009 | Raghavan | G06F 19/3418 |
| | | | 715/738 |
| 2012/0207274 A1* | 8/2012 | Yang | A61B 6/4233 |
| | | | 378/62 |
| 2013/0135272 A1 | 5/2013 | Park | |
| 2015/0181629 A1* | 6/2015 | Jun | H04W 76/021 |
| | | | 455/420 |
| 2016/0124406 A1* | 5/2016 | Kim | A61B 6/4411 |
| | | | 378/197 |
| 2016/0213346 A1* | 7/2016 | Benndorf | A61B 6/4405 |
| 2018/0146499 A1* | 5/2018 | Jun | A61B 5/00 |

FOREIGN PATENT DOCUMENTS

KR         200382643 B1     4/2005
KR     1020140057504 A     5/2014

\* cited by examiner

Fig. 8

<UNIT:mg>

| DIRECTION OF GRAVITY | X | Y | Z | REMARK |
|---|---|---|---|---|
| (a):POSITIVE X-AXIAL DIRECTION | 1000 | 0 | 0 | Full scale +/-2g |
| (b):NEGATIVE X-AXIAL DIRECTION | -1000 | 0 | 0 | |
| (c):POSITIVE Y-AXIAL DIRECTION | 0 | 1000 | 0 | |
| (d):NEGATIVE Y-AXIAL DIRECTION | 0 | -1000 | 0 | |
| (e):POSITIVE Z-AXIAL DIRECTION | 0 | 0 | 1000 | |
| (f):NEGATIVE Z-AXIAL DIRECTION | 0 | 0 | -1000 | |
| (g):POSITIVE X-AXIAL DIRECTION | 800 | 100 | -100 | |
| (h):NEGATIVE Z-AXIAL DIRECTION | -100 | 200 | -700 | |

Fig. 15

|  | Ceiling | Stand | Table |
|---|---|---|---|
| NORMAL | X | -X | Y |
| ABNORMAL | X | Z | Y |

DIRECTION OF GRAVITY

Fig. 16

| DIRECTION | ID | CAN ID |
|---|---|---|
| +X | 0001 | XXXXXXXX01 |
| -X | 0100 | XXXXXXXX100 |
| +Y | 0010 | XXXXXXXX10 |
| -Y | 0110 | XXXXXXXX110 |
| +Z | 0011 | XXXXXXXX11 |
| -Z | 0101 | XXXXXXXX101 |

PROCESSING BOARD, MEDICAL DIAGNOSTIC APPARATUS, AND METHOD OF CONTROLLING THE MEDICAL DIAGNOSTIC APPARATUS

CROSS-REFERENCE TO RELATED APPLICATION

This application claims priority from Korean Patent Application No. 10-2014-0152096, filed on Nov. 4, 2014, in the Korean Intellectual Property Office, the disclosure of which is incorporated herein by reference in its entirety.

BACKGROUND

1. Field

Apparatuses and methods consistent with exemplary embodiments relate to a processing board mounted on a medical diagnostic apparatus, the medical diagnostic apparatus, and a method of controlling the medical diagnostic apparatus.

2. Description of the Related Art

In general, medical diagnostic apparatuses acquire information of a patient and provide an image. The medical diagnostic apparatuses include an X-ray imaging apparatus, an ultrasonic diagnostic apparatus, a computed tomography (CT) apparatus, a magnetic resonance imaging (MRI) apparatus, and the like.

Among these medical diagnostic apparatuses, the X-ray imaging apparatus acquires an image of the inside of an object by using X-rays. The X-ray imaging apparatus non-invasively images the inside of the object by irradiating the object with X-rays and detecting X-rays having passed through the object. Thus, a medical X-ray imaging apparatus may be used to diagnose an injury or disease inside an object, which cannot be examined by external appearance.

The X-ray imaging apparatus includes a ceiling unit, which moves an X-ray source configured to generate X-rays and emit X-rays to an object toward the object, and a table and a stand on which an X-ray detector configured to detect X-rays having passed through the object is mounted. Meanwhile, a processing board is mounted on each of the ceiling unit, the table, and the stand, and the X-ray imaging apparatus includes a main processing board to control an overall operation of the processing boards of the ceiling unit, the table, and the stand.

The processing boards perform different roles in accordance with unique identifiers (IDs) allocated thereto by a user or the main processing board. For example, the processing board mounted on the ceiling unit may control the X-ray source to emit X-rays to the object, the processing board mounted on the table may control a height of the table, and the processing board mounted on the stand may control the X-ray detector to detect X-rays having passed through the object.

SUMMARY

Exemplary embodiments address at least the above problems and/or disadvantages and other disadvantages not described above. Also, the exemplary embodiments are not required to overcome the disadvantages described above, and may not overcome any of the problems described above.

Exemplary embodiments provide a processing board that senses its state, and automatically sets an identifier (ID) in accordance with the sensed state. The exemplary embodiments also provide a medical diagnostic apparatus that sets different IDs for processing boards in accordance with respective sensed states of the processing boards, and provides the set IDs to a main processing board, and a method of controlling the medical diagnostic apparatus.

According to an aspect of an exemplary embodiment, there is provided a processing board mounted on a medical diagnostic apparatus, the processing board including a sensor configured to sense at least one selected from the group consisting of an installation position, an installation direction, and a power consumption of the processing board. The processing board further includes a controller configured to set an identifier (ID) of the processing board based on an output signal of the sensor.

The processing board may further include a communication interface configured to transmit the ID to another processing board.

The communication interface may include a controller area network (CAN) communication interface configured to transmit the ID to the other processing board via a CAN communication network.

The sensor may include at least one selected from the group consisting of an accelerometer, a magnetic sensor, a height sensor, and a current sensor.

The accelerometer may be configured to sense a direction of gravity of the processing board with a strength greater than a threshold.

The processing board may further include a switch configured to output a signal based on a turn-on or turn-off input.

The processing board may further include a storage configured to store one or more IDs respectively corresponding to one or more output signals of the sensor, and the controller may be further configured to find an ID corresponding to the output signal of the sensor among the one or more IDs, and set the found ID as the ID of the processing board.

The medical diagnostic apparatus may be one among an ultrasonic diagnostic apparatus, a magnetic resonance imaging apparatus, and a computed tomography apparatus.

The processing board may further include a communication interface configured to transmit a firmware update request of the processing board to another processing board.

The communication interface may be further configured to receive a firmware update file of the processing board from the other processing board.

According to an aspect of another exemplary embodiment, there is provided a medical diagnostic apparatus including a processing board mounted on the medical diagnostic apparatus, the processing board being configured to sense at least one selected from the group consisting of an installation position, an installation direction, and a power consumption of the processing board. The processing board is further configured set an identifier (ID) of the processing board based on a sensed result. The medical diagnostic apparatus further includes a main processing board configured to receive the ID from the processing board.

The processing board may be further configured to store an expected value of the at least one selected from the group consisting of the installation position, the installation direction, and the power consumption, and determine whether an installation error of the processing board occurs by comparing the sensed result with the expected value.

The medical diagnostic apparatus may further include a workstation configured to receive the ID from the main processing board.

The medical diagnostic apparatus may further include an X-ray source configured to generate X-rays, and emit the X-rays to an object, a ceiling apparatus configured to move the X-ray source toward the object, an X-ray detector configured to detect X-rays having passed through the object, and a table and a stand on which the X-ray detector is mounted.

The processing board may include a first processing board, a second processing board, and a third processing board, the first processing board may be mounted on the ceiling apparatus, the second processing board may be mounted on the stand, and the third processing board may be mounted on the table.

According to an aspect of another exemplary embodiment, there is provided a method of controlling a medical diagnostic apparatus, the method including sensing at least one selected from the group consisting of an installation position, an installation direction, and a power consumption of a processing board mounted on the medical diagnostic apparatus. The method further includes setting an identifier (ID) of the processing board based on a sensed result, and transmitting the ID to another processing board.

The sensing may include sensing a direction of gravity of the processing board with a strength greater than a threshold.

The method may further include transmitting a firmware update request of the processing board to the other processing board.

The method may further include receiving a firmware update file of the processing board from the other processing board.

According to an aspect of another exemplary embodiment, there is provided a processing board mounted on a medical diagnostic apparatus, the processing board including a sensor configured to sense an output value of at least one among a direction of gravity, a direction of a magnetic force, a height from a floor, and a current of the processing board. The processing board further includes a controller configured to determine whether an installation error of the processing board occurs based on the output value.

The controller may be further configured to determine whether the output value is different than an expected value of the at least one among the direction of gravity, the direction of the magnetic force, the height from the floor, and the current of the processing board, and determine that the installation error occurs in response to the controller determining that the output value is different than the expected value.

The processing board may further include a switch configured to output a value based on a turn-on or turn-off input, and the controller may be further configured to determine an identifier of the processing board based on the output value of the sensor, determine whether the identifier is different than the output value of the switch, and determine that the installation error occurs in response to the controller determining that the identifier is different than the output value of the switch.

The controller may be further configured to set an identifier of the processing board based on the output value in response to the controller determining that the installation error does not occur.

BRIEF DESCRIPTION OF THE DRAWINGS

The above and/or other aspects will be more apparent by describing certain exemplary embodiments with reference to the accompanying drawings in which:

FIGS. 6 to 12 are diagrams illustrating X-ray imaging apparatuses provided with a processing board including a sensing portion according to exemplary embodiments;

FIG. 15 is a table illustrating a method of determining an installation error of a processing board based on output values of a sensor implemented using an accelerometer according to an exemplary embodiment;

FIG. 16 is a table illustrating controller area network (CAN) communication identifiers (IDs) corresponding to output values of a sensor implemented using an accelerometer according to an exemplary embodiment.

DETAILED DESCRIPTION OF THE EXEMPLARY EMBODIMENTS

Figure 1:
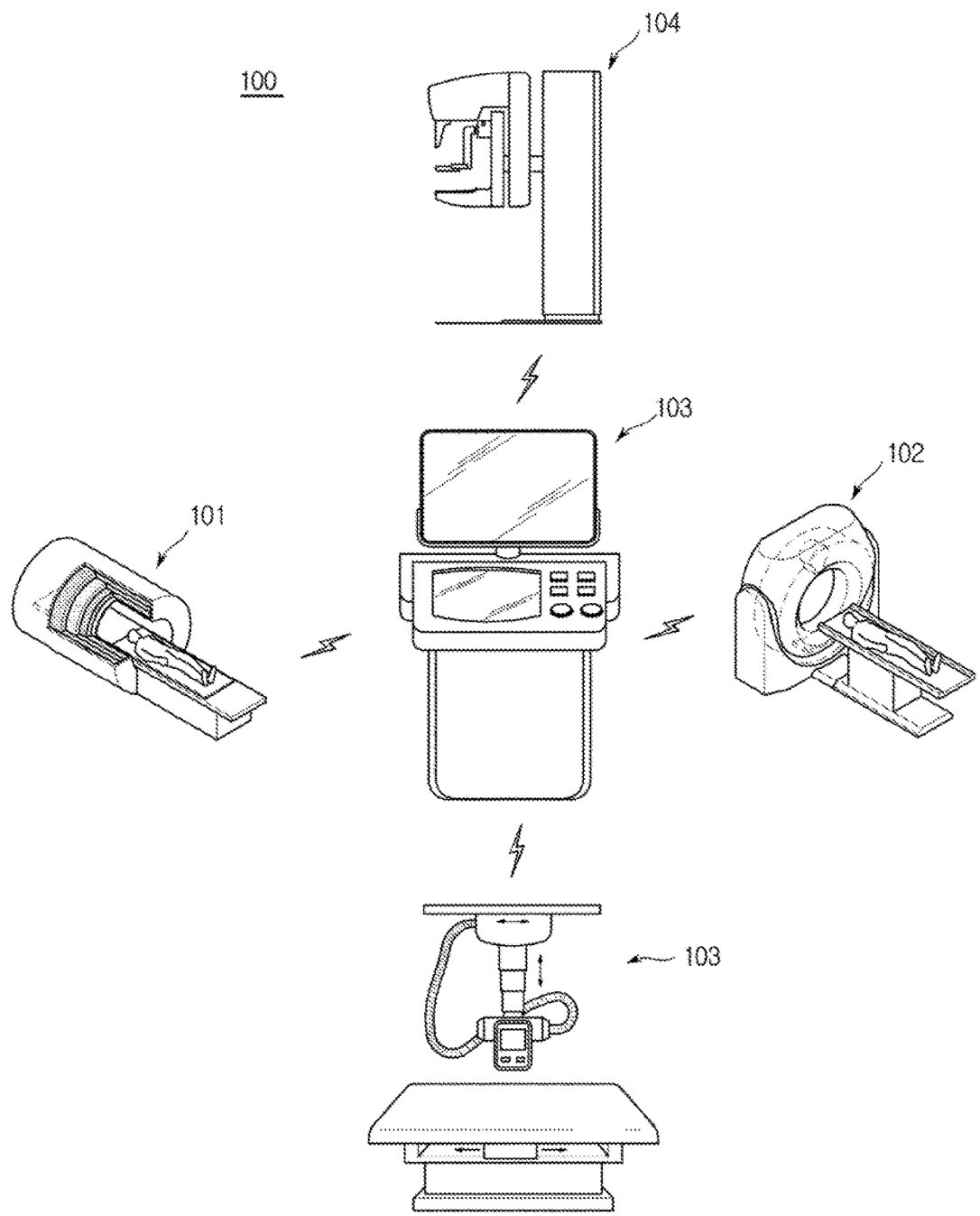
FIG. 1 is a conceptual diagram schematically illustrating a medical diagnostic apparatus according to an exemplary embodiment.

Exemplary embodiments are described in greater detail herein with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that the terms such as "unit," "-er (-or)," and "module" described in the specification refer to an element for performing at least one function or operation, and may be implemented in hardware, software, or the combination of hardware and software.

FIG. 1 is a conceptual diagram schematically illustrating a medical diagnostic apparatus 100 according to an exemplary embodiment.

Referring to FIG. 1, the medical diagnostic apparatus 100 includes image capturing apparatuses 101, 102, 103, and 104 configured to capture an inner or outer image of an object ob, and a workstation 170 configured to match images received from the image capturing apparatuses 101, 102, 103, and 104.

As illustrated in FIG. 1, the image capturing apparatuses 101, 102, 103, and 104 may be disposed to be spaced apart from the workstation 170 of the medical diagnostic apparatus 100 by a predetermined distance. The image capturing apparatuses 101, 102, 103, and 104 may also be connected to the workstation 170 via various wired or wireless communication protocols.

For example, the image capturing apparatuses 101, 102, 103, and 104 may respectively perform data communications with the workstation 170 via The Digital Imaging and Communications in Medicine (DICOM) Standard, without being limited thereto. Also, the image capturing apparatuses 101, 102, 103, and 104 may be connected to the workstation 170 via mobile communication protocols such as Global System for Mobile Communication (GSM), Code Division Multiple Access (CDMA), Wideband Code Division Multiple Access (WCDMA), Time Division Multiple Access (TDMA), and Long Term Evolution (LTE), and short-distance communication protocols such as Wireless Local Access Network (WLAN), Bluetooth, Zigbee, and Near Field Communication (NFC).

In this regard, each of the image capturing apparatuses 101, 102, 103, and 104 acquires internal images of the object ob by using X-rays, magnetic resonance, or ultrasound. For example, the image capturing apparatuses 101, 102, 103, and 104 may acquire the internal images of the object ob by using X-rays in the same manner as in a Computed Tomography (CT) apparatus, a Positron Emission Tomography (PET) apparatus, a Single Photon Emission Computed Tomography (SPECT) apparatus, or a Mammography apparatus. Also, the image capturing apparatuses 101, 102, 103, and 104 may acquire the internal images of the object ob by using X-rays in the same manner as in an X-ray imaging apparatus or by using ultrasound.

As described above, the image capturing apparatuses 101, 102, 103, and 104 may acquire images of the object ob by using various methods.

Hereinafter, an X-ray imaging apparatus generating an image by using X-rays will be described as the medical diagnostic apparatus 100 for descriptive convenience. However, exemplary embodiments are not limited thereto, and a method of acquiring images may be substituted or modified by any other method of acquiring internal images. Furthermore, images may be generated by applying various other methods of acquiring images.

Figure 2:
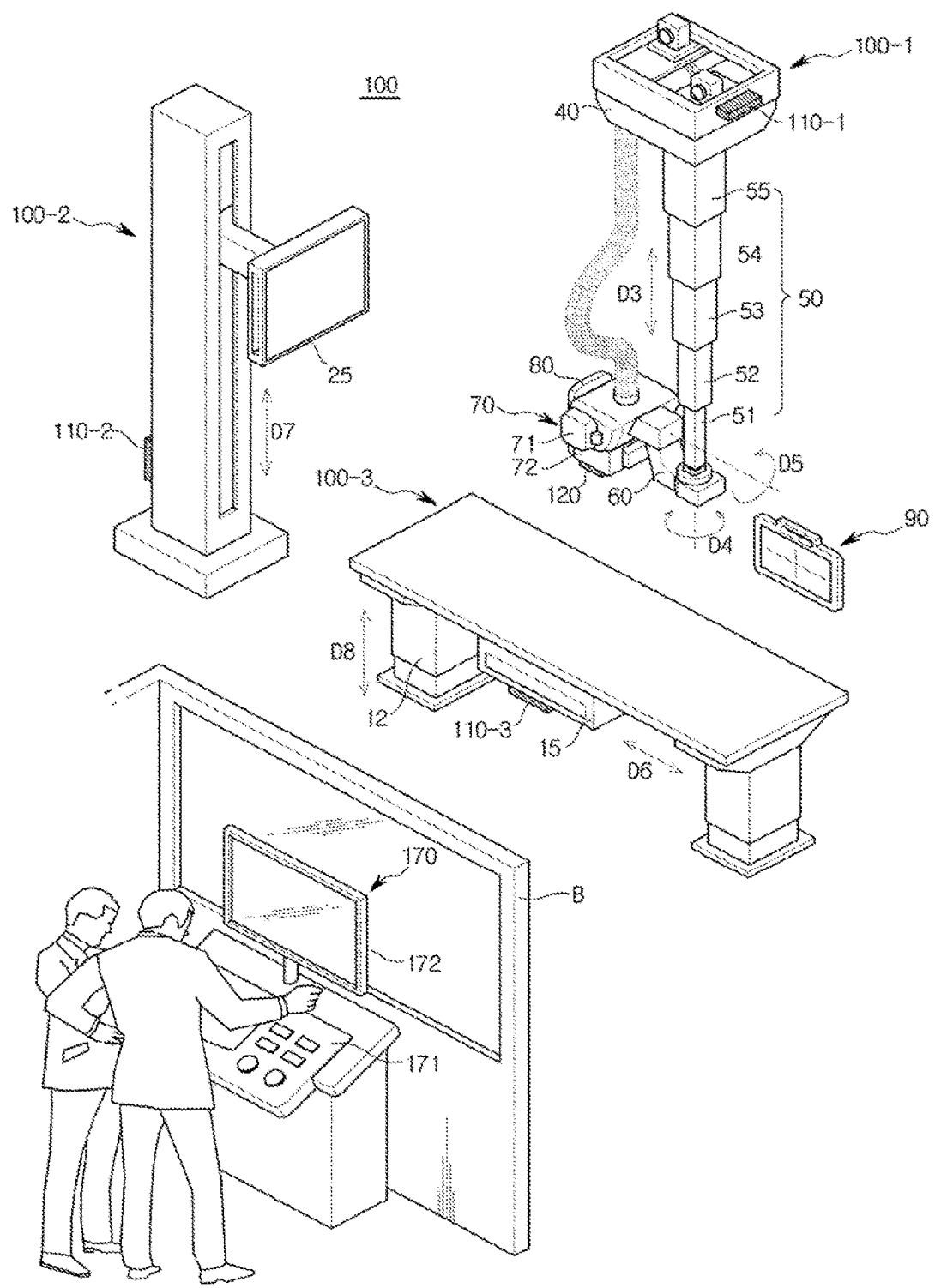
FIG. 2 is a perspective view illustrating an appearance of an X-ray imaging apparatus according to an exemplary embodiment.
Figure 3:
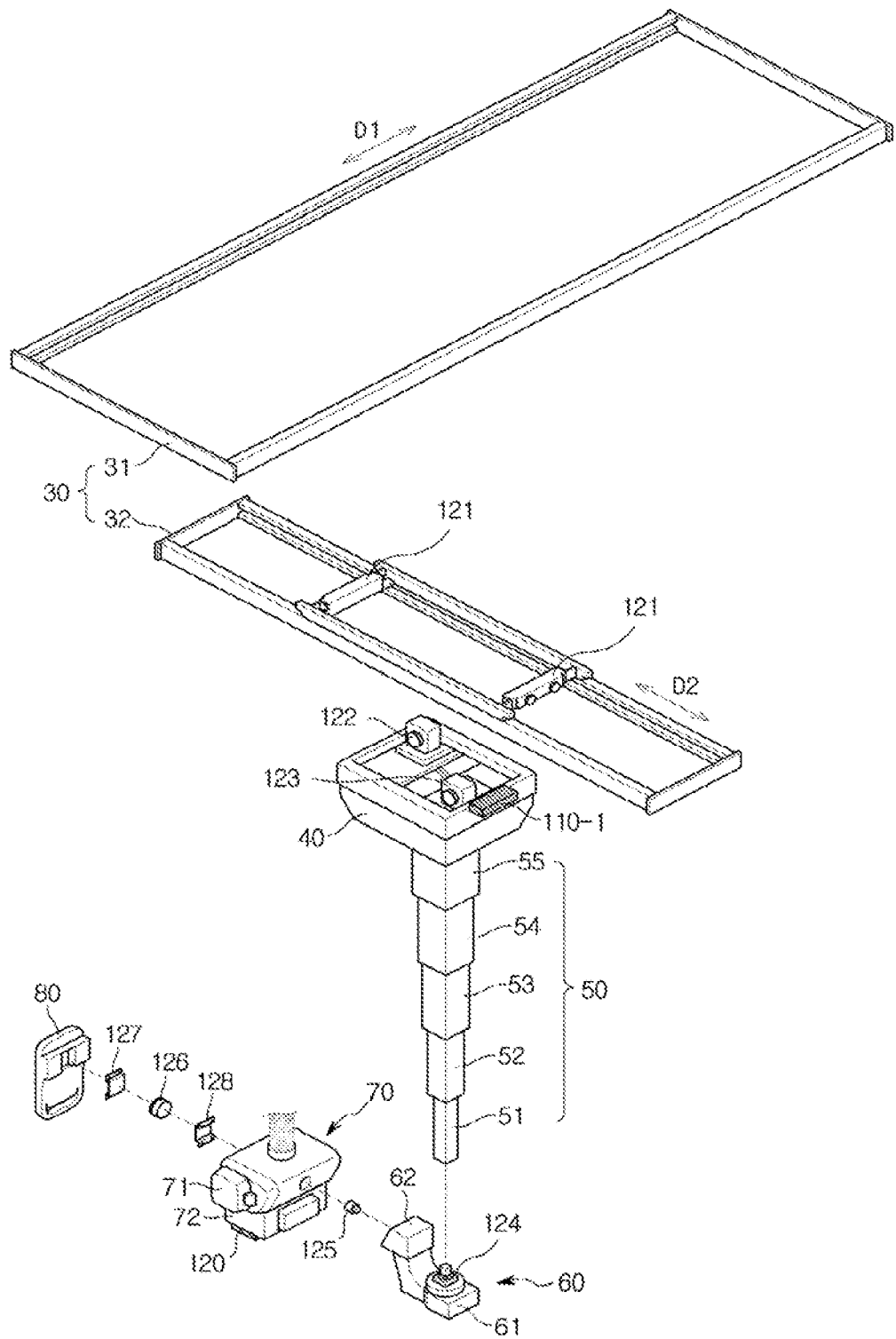
FIG. 3 is an exploded perspective view illustrating the X-ray imaging apparatus of FIG. 2.

FIG. 2 is a perspective view illustrating an appearance of an X-ray imaging apparatus 100 according to an exemplary embodiment. FIG. 3 is an exploded perspective view illustrating the X-ray imaging apparatus 100 of FIG. 2.

Referring to FIGS. 2 and 3, the X-ray imaging apparatus 100 includes a ceiling apparatus 100-1 disposed on a ceiling of an X-ray room to move an X-ray source 70, which emits X-rays to the object ob, toward the object ob. The X-ray imaging apparatus 100 further includes a table 100-3, the workstation 170, and a stand 100-2 on which an X-ray detector 90, which detects X-rays having passed through the object ob, is mounted.

The ceiling apparatus 100-1 includes a guide rail 30, a movable carriage 40, a post frame 50, actuators 121 to 125, the X-ray source 70, and a manipulation apparatus 80. The guide rail 30, the movable carriage 40, the post frame 50, and the like are used to move the X-ray source 70 toward the object ob.

The guide rail 30 includes a first guide rail 31 and a second guide rail 32, which are disposed at a predetermined angle. The first guide rail 31 and the second guide rail 32 may respectively extend in directions perpendicular to each other.

The first guide rail 31 is mounted on the ceiling of an examination room in which the X-ray imaging apparatus 100 is located. The second guide rail 32 is located at a bottom of the first guide rail 31 to be slidably coupled to the first guide rail 31. The first guide rail 31 may be provided with a roller that moves along the first guide rail 31. The second guide rail 32 may move along the first guide rail 31 in a state of being coupled to the roller.

An extending direction of the first guide rail 31 is defined as a first direction D1, and an extending direction of the second guide rail 32 is defined as a second direction D2. Thus, the first direction D1 and the second direction D2 may be perpendicular to each other and parallel to the ceiling of the examination room.

The movable carriage 40 is installed at a bottom of the second guide rail 32 to move along the second guide rail 32. The movable carriage 40 may be provided with a roller to move along the second guide rail 32. Thus, the movable carriage 40 may move in the first direction D1 together with the second guide rail 32 and in the second direction D2 along the second guide rail 32.

The post frame 50 is fixed to the movable carriage 40 and located at a bottom of the movable carriage 40. The post frame 50 includes a plurality of posts 51, 52, 53, 54, and 55. The plurality of posts 51, 52, 53, 54, and 55 are connected to have a telescopic configuration such that the post frame 50 may increase or decrease in length in a vertical direction of the examination room in a state of being fixed to the movable carriage 40.

A direction in which the length of the post frame 50 increases or decreases is defined as a third direction D3. Thus, the third direction D3 may be perpendicular to the first direction D1 and the second direction D2, respectively.

The X-ray source 70 is a device that emits X-rays toward the object ob. As used herein, the object ob may refer to a living body of a human or an animal, without being limited thereto, and any object, an inner structure of which may be imaged by the X-ray imaging apparatus 100, may also be used as the object ob. Hereinafter, a human body will be described as the object ob for descriptive convenience.

The X-ray source 70 includes an X-ray tube 71 configured to generate X-rays, and a collimator 72 configured to guide the generated X-rays toward the object ob. The X-ray tube 71 will be described in more detail later.

A rotating joint 60 is disposed between the X-ray source 70 and the post frame 50. The rotating joint 60 couples the X-ray source 70 to the post frame 50, and supports a load applied to the X-ray source 70. The rotating joint 60 includes a first rotating joint 61 connected to a lower post 51 of the post frame 50, and a second rotating joint 62 connected to the X-ray source 70.

The first rotating joint 61 is installed to be rotated about a central axis of the post frame 50 that extends in the vertical direction of the examination room. Thus, the first rotating joint 61 may be rotated on a plane perpendicular to the third direction D3. In this regard, a rotating direction of the first rotating joint 61 is defined as a fourth direction D4, which is a rotating direction of an axis parallel to the third direction D3.

The second rotating joint 62 is installed to be rotated on a plane perpendicular to the ceiling of the examination room. Thus, the second rotating joint 62 may be rotated in a rotating direction of an axis parallel to the first direction D1 or the second direction D2. In this regard, the rotating direction of the second rotating joint 62 is defined as a fifth direction D5, which is a rotating direction of an axis extending in the first direction D1 or the second direction D2. The X-ray source 70 may be rotated in the fourth direction D4 and the fifth direction D5 in a state of being coupled to the rotating joint 60. In addition, the X-ray source 70 may linearly move in the first direction D1, the second direction D2, and the third direction D3 in a state of being coupled to the post frame 50 via the rotating joint 60.

The actuators 121 to 125 are provided to move the X-ray source 70 in the first direction D1 to the fifth direction D5.

Each of the actuators 121 to 125 may include a motor, which may be an electric motor, and a motor driver configured to drive the motor.

The actuators 121 to 125 include first, second, third, fourth, and fifth actuators 121, 122, 123, 124, and 125 corresponding to respective directions D1, D2, D3, D4, and D5. The actuators 121 to 125 may be located at different positions, respectively, for design convenience. For example, the first actuator 121 that moves the second guide rail 32 in the first direction D1 is disposed around the first guide rail 31, the second actuator 122 that moves the movable carriage 40 in the second direction D2 is disposed around the second guide rail 32, and the third actuator 123 that increases or decrease the length of the post frame 50 in the third direction D3 is disposed inside the movable carriage 40. Also, the fourth actuator 124 that rotates the X-ray source 70 in the fourth direction D4 is disposed around the first rotating joint 61, and the fifth actuator 125 that rotates the X-ray source 70 in the fifth direction D5 is disposed around the second rotating joint 62. In this regard, the first actuator 121, the second actuator 122, and the third actuator 123, which move the movable carriage 40, are defined as a carriage actuator 120.

Each of the first to fifth actuators 121, 122, 123, 124, and 125 may be connected to a power transmission apparatus configured to linearly or rotatably move the X-ray source 70 in the first direction D1 to fifth direction D5. Belts and pulleys, chains and sprockets, shafts, and any other components commonly used in the art may be used as the power transmission apparatus.

The manipulation apparatus 80 providing a user interface is mounted on one side of the X-ray source 70 using physical connectors 126 to 128. As used herein, the term "user" refers to medical professionals performing diagnosis of the object ob by using the X-ray imaging apparatus 100, such as doctors, X-ray technicians, and nurses. However, the user is not limited thereto, and anyone using the X-ray imaging apparatus 100 may also be regarded as the user.

The ceiling apparatus 100-1 further includes a central processing unit (CPU) 112a (FIG. 14), which may be implemented using a microprocessor, to control the guide rail 30, the movable carriage 40, the post frame 50, the actuators 120, 124, and 125, and the X-ray source 70. The CPU 112a is mounted on a printed circuit board (PCB) as an embedded processing board 110-1.

A processing board 110 may also be embedded in the stand 100-2 and the table 100-3, and perform different functions depending on embedded positions. In addition to the embedded forms, the processing board 110 may also be mounted on outer surfaces of the stand 100-2 and the table 100-3 as a processing board 110-2 and a processing board 110-3 illustrated in FIG. 2. The processing board 110 will be descried in more detail later.

Figure 4:
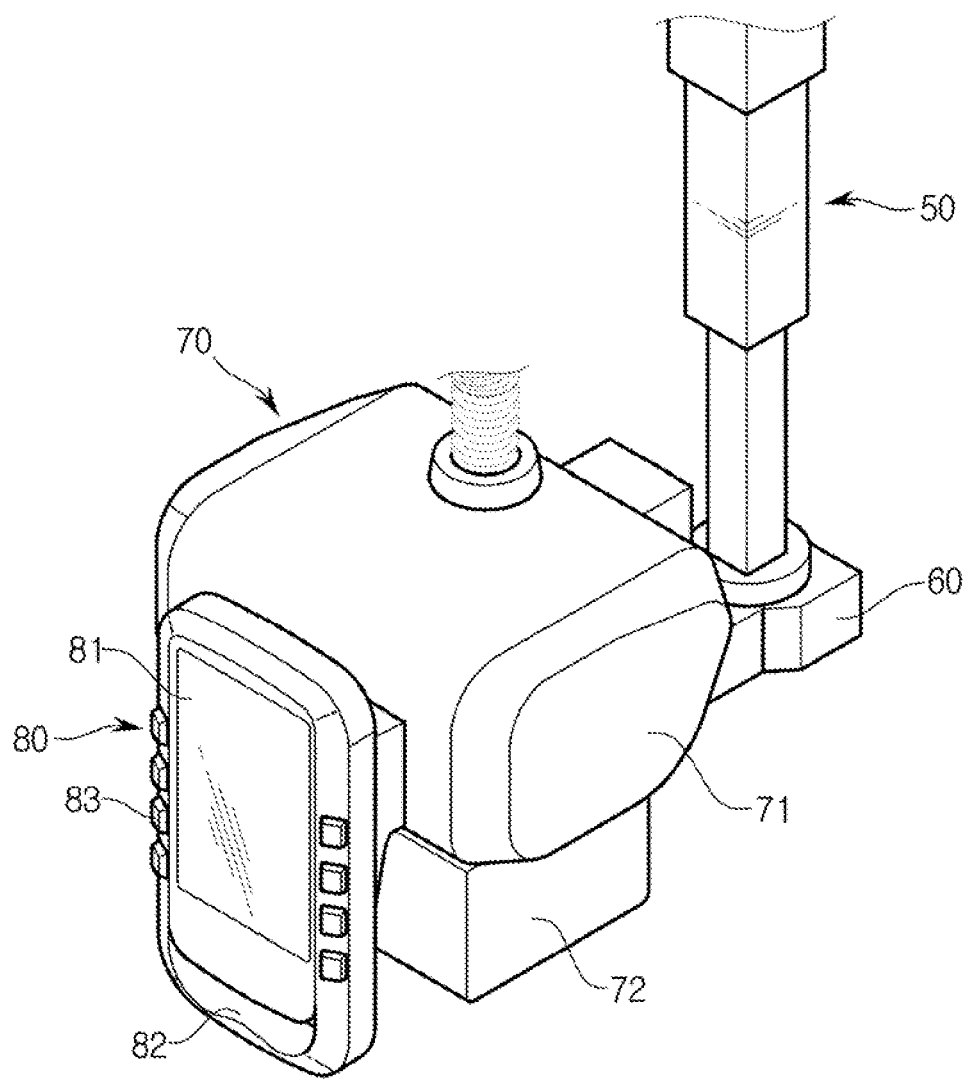
FIG. 4 is a perspective view illustrating a manipulation apparatus of the X-ray imaging apparatus of FIG. 2.

FIG. 4 is a perspective view illustrating the manipulation apparatus 80 of the X-ray imaging apparatus 100 of FIG. 2.

As illustrated in FIG. 4, the manipulation apparatus 80 includes a button 83 and a display panel 81. The user may input various information regarding X-ray imaging, or manipulate each device, by pressing the button 83 or by touching the display panel 81. The display panel 81 may be, for example, a cathode ray tube (CRT), a digital light processing (DLP) panel, a plasma display penal (PDP), a liquid crystal display (LCD) panel, an electro luminescence (EL) panel, an electrophoretic display (EPD) panel, an electrochromic display (ECD) panel, a light emitting diode (LED) panel, or an organic light emitting diode (OLED) panel, without being limited thereto.

The manipulation apparatus 80 also includes a handle 82 gripped by the user. That is, the user may linearly move the X-ray source 70 in the first direction D1 to the third direction D3, or may rotatably move the X-ray source 70 in the fourth direction D4 and the fifth direction D5, by gripping the handle 82 of the manipulation apparatus 80 and applying force or torque thereto. Although the handle 82 is provided at a lower portion of the manipulation apparatus 80 in FIG. 3, the handle 82 may also be provided at any other portion of the manipulation apparatus 80.

Figure 5:
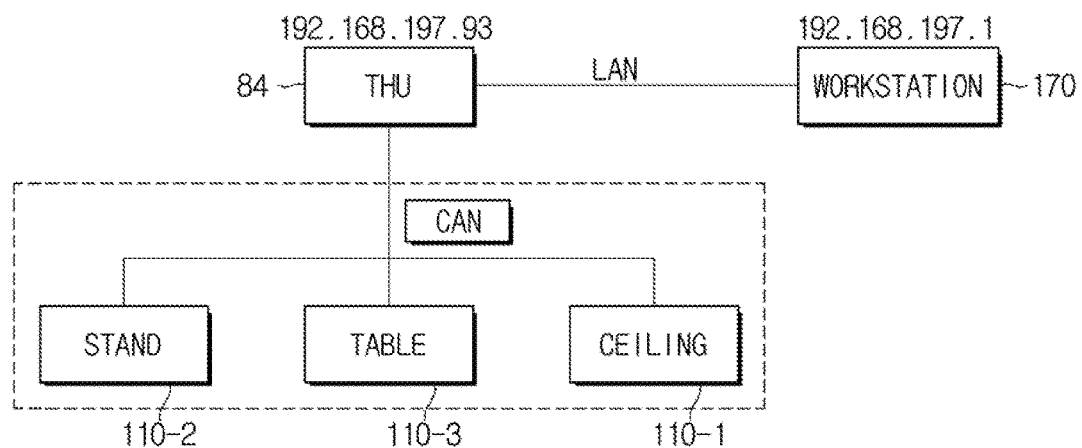
FIG. 5 is a schematic diagram illustrating a connection among a main processing board, a workstation, and processing boards according to an exemplary embodiment.

The manipulation apparatus 80 may include a CPU implemented using a microprocessor, a graphic processing unit (GPU), and various types of storage devices, and these devices may be mounted on a PCB as an embedded processing board 84 (FIG. 5). That is, because the manipulation apparatus 80 includes the processing board 84 and is disposed at one side of the X-ray source 70, the manipulation apparatus 80 may be referred to as "Tube Head Board" or "THU". Hereinafter, the processing board 84 included in the manipulation apparatus 80 will be referred to as a main processing board 84 for descriptive convenience.

The main processing board 84 included in the manipulation apparatus 80 is connected to the processing boards 110-1, 110-2, and 110-3 respectively mounted on the ceiling apparatus 100-1, the stand 100-2, and the table 100-3, thereby controlling an overall operation of the processing boards 110-1, 110-2, and 110-3.

Referring back to FIG. 2, the workstation 170 includes an input interface 171 and a display 172, and provides a user interface together with the manipulation apparatus 80. Thus, the user may input various information regarding X-ray imaging, or manipulate various devices through the workstation 170.

For example, the user may set conditions for X-ray imaging in accordance with a target region or may input a command to move the movable carriage 40 or the X-ray source 70 or a command to start X-ray imaging via the workstation 170. In addition, the user may confirm images acquired by X-ray imaging through the workstation 170.

The input interface 171 may include a hardware input device to input a user's command such as buttons, switches, a keyboard, a mouse, a track-ball, levers, a handle, or a stick. The input interface 210 is disposed at an upper portion of the workstation 170 in FIG. 2. However, in case of a foot switch and a foot pedal, the input interface 210 may be disposed at a lower portion of the workstation 170.

The input interface 171 may also include a graphical user interface (GUI) such as a touch pad, i.e., a software input device, to input a user's command. The touch pad may be implemented using a touch screen panel (TSP) to constitute a layered structure with the display 172, which will be described later.

The display 172, like the display panel 81 of the manipulation apparatus 80, may be a cathode ray tube (CRT), a digital light processing (DLP) panel, a plasma display penal (PDP), a liquid crystal display (LCD) panel, an electro luminescence (EL) panel, an electrophoretic display (EPD) panel, an electrochromic display (ECD) panel, a light emitting diode (LED) panel, or an organic light emitting diode (OLED) panel, without being limited thereto.

When the display 172 is implemented using a TSP constituting a layered structure with the touch pad as described above, the display 172 may also be used as an input device as well as a display.

In addition, a PCB may be embedded in the workstation 170 as a processing board including various processing devices such as a CPU and GPU and various types of storage devices. Thus, the workstation 170 may perform various determinations for operations of the X-ray imaging apparatus 100, or generate various control signals, by accommodating main components of the X-ray imaging apparatus 100.

Because a barrier B to block X-rays is disposed between the workstation 170 and the examination room, the user may input information or manipulate devices without being exposed to X-rays even while performing X-ray imaging by using the barrier B.

The X-ray detector 90 is a device configured to detect X-rays that have passed through the object ob. The X-ray detector 90 may be mounted on the table 100-3 or the stand 100-2 while performing X-ray imaging.

The table 100-3 may be provided with a first mounting portion 15 on which the X-ray detector 90 is mounted, and the first mounting portion 15 may move in a lengthwise direction of the table 100-3.

In the same manner, the stand 100-2 is provided with a second mounting portion 25 on which the X-ray detector 90 is mounted, and the second mounting portion 25 may move in a lengthwise direction of the stand 100-2.

In this regard, the lengthwise direction of the table 100-3 is defined as a sixth direction D6, and the lengthwise direction of the stand 100-2 is defined as a seventh direction D7. While the first mounting portion 15 or the second mounting portion 25 on which the X-ray detector 90 is mounted moves along the sixth direction D6 or the seventh direction D7, an entire or partial region of the object ob of interest may be imaged.

The table 100-3 includes a support 12 that supports the table 100-3 and adjusts a height of the table 100-3, and the support 12 may be provided with a table actuator to vertically move the support 12. Here, a vertical direction of the support 12 is defined as an eighth direction D8.

In this case, the stand 100-2 and the table 100-3 may further include a CPU implemented using a microprocessor, respectively, and the CPU may be mounted on a PCB as the embedded processing board 110-2 or 110-3. These processing boards may be respectively embedded in the stand 100-2 and the table 100-3, and perform different functions. The processing board 110 will be described in more detail later.

The appearance of the X-ray imaging apparatus 100 is described. Hereinafter, the processing boards respectively mounted on the ceiling apparatus 100-1, the stand 100-2, and the table 100-3 will be described in detail.

Hereinafter, the processing board 110 mounted on the ceiling apparatus 100-1 is referred to as the first processing board 110-1, the processing board 110 mounted on the stand 100-2 is referred to as the second processing board 110-2, and the processing board 110 mounted on the table 100-3 is referred to as the third processing board 110-3, for descriptive convenience.

FIG. 5 is a schematic diagram illustrating a connection among the main processing board 84, the workstation 170, and the processing boards 110-1, 110-2, and 110-3 according to an exemplary embodiment.

Referring to FIG. 5, the main processing board 84 (THU) controls the first to third processing boards 110-1, 110-2, and 110-3 respectively mounted on the ceiling apparatus 100-1, the stand 100-2, and the table 100-3, and transmits data received from the first to third processing boards 110-1, 110-2, and 110-3 to the workstation 170. The main processing board 84 is connected with the first to third processing board 110-1, 110-2, and 110-3 respectively mounted on the ceiling apparatus 100-1, the stand 100-2, and the table 100-3 via a controller area network (CAN). The main processing board 84 is connected with the workstation 170 via a local area network (LAN).

However, a communication network connecting the devices is not limited thereto and examples of the communication network may include a wired communication network, a wireless communication network, a LAN, or any combination thereof. The wired communication network includes a wired Ethernet network, a wide area network (WAN), a value added network (VAN), and a controller area network (CAN). The wireless communication network may access a wireless communication network at a region where an access point (AP) is located to be connected to the AP. The wireless communication network supports wireless LAN standard IEEE 802 11x of The Institute of Electrical and Electronics Engineers (IEEE). The LAN includes Bluetooth, Bluetooth low energy (BLE), Infrared Data Association (IrDA), Wi-Fi, ultra wideband (UWB), near field communication (NFC), Zigbee, and the like.

When the main processing board 84 is connected with the first to third processing boards 110-1, 110-2, and 110-3 via the communication network, the first to third processing boards 110-1, 110-2, and 110-3 have unique identifiers (IDs) such that the main processing board 84 distinguishes one of the first to third processing boards 110-1, 110-2, and 110-3 from the others.

Although the unique IDs of the first to third processing boards 110-1, 110-2, and 110-3 may be manually set by the user, the first to third processing boards 110-1, 110-2, and 110-3 may automatically set their own IDs according to an exemplary embodiment. In this case, the first to third processing boards 110-1, 110-2, and 110-3 set their IDs differently in accordance with respective mounted states thereof on the X-ray imaging apparatus 100. Each of the first to third processing boards 110-1, 110-2, and 110-3 includes a sensing portion 111 (FIG. 14) configured to sense the mounted states of the first to third processing boards 110-1, 110-2, and 110-3.

FIGS. 6 to 12 are diagrams illustrating the X-ray imaging apparatuses 100 provided with a processing board including a sensing portion according to exemplary embodiments.

Referring to FIGS. 6 and 9 to 11, the first to third processing boards 110-1, 110-2, and 110-3 are mounted on outer surfaces of the ceiling apparatus 100-1, the stand 100-2, and the table 100-3, respectively. However, the first to third processing boards 110-1, 110-2, and 110-3 may also be installed inside the ceiling apparatus 100-1, the stand 100-2, and the table 100-3, respectively. Hereinafter, the first to third processing boards 110-1, 110-2, and 110-3 mounted as illustrated in FIGS. 6 and 9 to 11 will be described by way of example for descriptive convenience.

Referring to FIGS. 6 and 9 to 11, each of the first to third processing boards 110-1, 110-2, and 110-3 according to exemplary embodiments includes the sensing portion 111. In detail, each of the first processing board 110-1 mounted on the ceiling apparatus 100-1, the second processing board 110-2 mounted on the stand 100-2, and the third processing board 110-3 mounted on the table 100-3 includes the sensing portion 111 that senses at least one of installation positions and installation directions thereof on the ceiling apparatus 100-1, the stand 100-2, or the table 100-3, and power consumptions of the first to third processing boards 110-1, 110-2, and 110-3.

Figure 6:
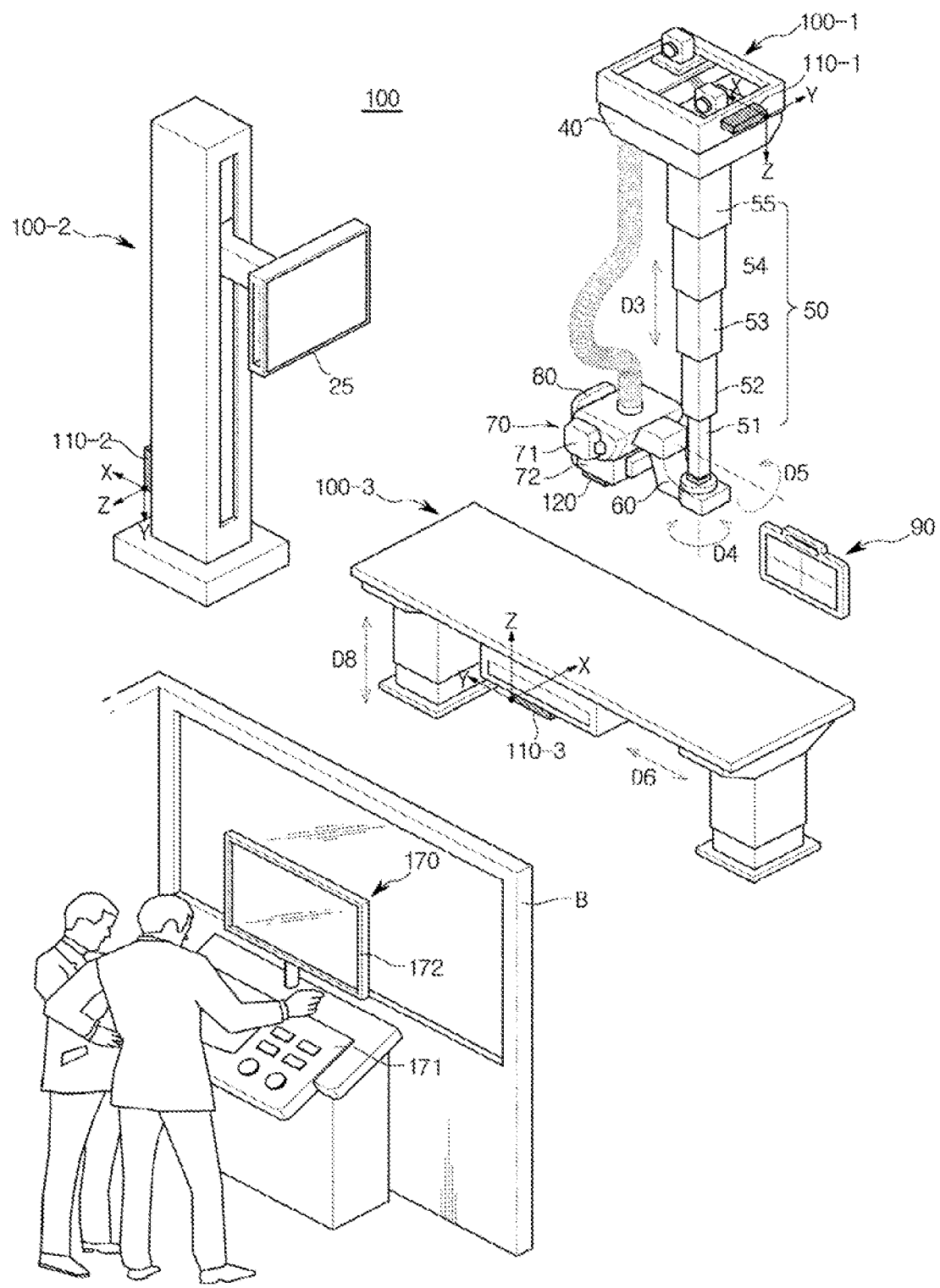

Referring to FIG. 6, the sensing portion 111 is implemented using an accelerometer, and the accelerometer outputs different signals in accordance with the installation positions or installation directions of the first to third processing boards 110-1, 110-2, and 110-3 respectively mounted on the ceiling apparatus 100-1, the stand 100-2, and the table 100-3.

Figure 7:
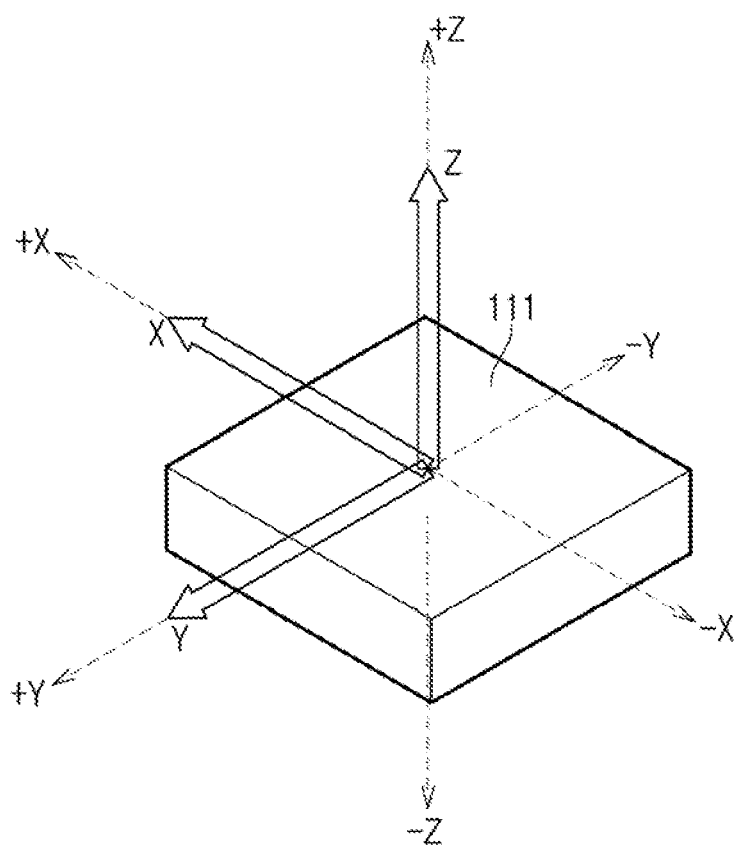

FIG. 7 is a diagram of coordinates illustrating a direction of a force sensed by an accelerometer of the sensing portion 111. FIG. 8 is a table illustrating output values generated when the accelerometer senses directions of gravity.

For example, when a coordinate system of the accelerometer is formed by X-, Y-, and Z-axes as illustrated in FIGS. 6 and 7, the accelerometer senses a force acting in one direction of the X-axis as a positive X-axial direction, a force acting in the opposite direction of the X-axis as a negative X-axial direction, a force acting in one direction of the Y-axis as a positive Y-axial direction, a force acting in the opposite direction of the Y-axis as a negative Y-axial direction, a force acting in one direction of the Z-axis as a positive Z-axial direction, and a force acting in the opposite direction of the Z-axis as a negative Z-axial direction.

When the first processing board 110-1 is mounted on the ceiling apparatus 100-1 such that a coordinate system of the first processing board 110-1 of the ceiling apparatus 100-1 is formed by the third direction D3, as the Z-axis, and the first direction D1, as the Y-axis, based on FIGS. 2 to 3 and 6, the accelerometer senses the direction of gravity as the positive Z-axial direction.

Also, when the second processing board 110-2 is mounted on the stand 100-2 such that a coordinate system of the second processing board 110-2 of the stand 100-2 is formed by the seventh direction D7, as the Y-axis, and the first direction D1, as the Z-axis, based on FIGS. 2 to 3 and 6, the accelerometer senses the direction of gravity as the positive Y-axial direction.

In addition, when the third processing board 110-3 is mounted on the table 100-3 such that a coordinate system of the third processing board 110-3 of the table 100-3 is formed by the eighth direction D8, as the Z-axis, and the first direction D1, as the X-axis, based on FIGS. 2 to 3 and 6, the accelerometer senses the direction of gravity as the negative Z-axial direction.

When the accelerometer senses the direction of gravity as described above, the accelerometer generates output values as shown in FIG. 8. In detail, when the processing board 110 is mounted such that a vertical downward direction is set as the positive X-axial direction, the accelerometer senses gravity to generate output values as shown in (a) of FIG. 8. Also, when the processing board 110 is mounted such that the vertical downward direction is set as the negative X-axial direction, the accelerometer senses gravity to generate output values as shown in (b) of FIG. 8.

When the processing board 110 is mounted such that the vertical downward direction is set as the positive Y-axial direction, the accelerometer senses gravity to generate output values as shown in (c) of FIG. 8. When the processing board 110 is mounted such that the vertical downward direction is set as the negative Y-axial direction, the accelerometer senses gravity to generate output values as shown in (d) of FIG. 8.

When the processing board 110 is mounted such that the vertical downward direction is set as the positive Z-axial direction, the accelerometer senses gravity to generate output values as shown in (e) of FIG. 8. When the processing board 110 is mounted such that the vertical downward direction is set as the negative Z-axial direction, the accelerometer senses gravity to generate output values as shown in (f) of FIG. 8.

Meanwhile, the vertical downward direction may include elements of both the X- and Y-axial directions, elements of both the Y- and Z-axial directions, elements of both the Z- and X-axial directions, or elements of all of the X-, Y, and Z-axial directions. In this case, the accelerometer senses a direction having an output value greater than a predetermined threshold as the direction of gravity.

For example, when the processing board 110 is mounted such that the vertical downward direction includes elements of all of the X-, Y-, and Z-axial directions, the accelerometer may generate output values as shown in (g) of FIG. 8, and sense the X-axial direction having an absolute value of 700 mg or more as the direction of gravity. In addition, when the processing board 110 is mounted such that the vertical downward direction includes elements of all of the X-, Y-, and Z-axial directions, the accelerometer may generate output values as shown in (h) of FIG. 8, and sense the negative Z-axial direction having an absolute value of 700 mg or more as the direction of gravity.

Meanwhile, the output values are not limited to those listed in the table of FIG. 8, and may vary in accordance with performance of the accelerometer.

Figure 9:
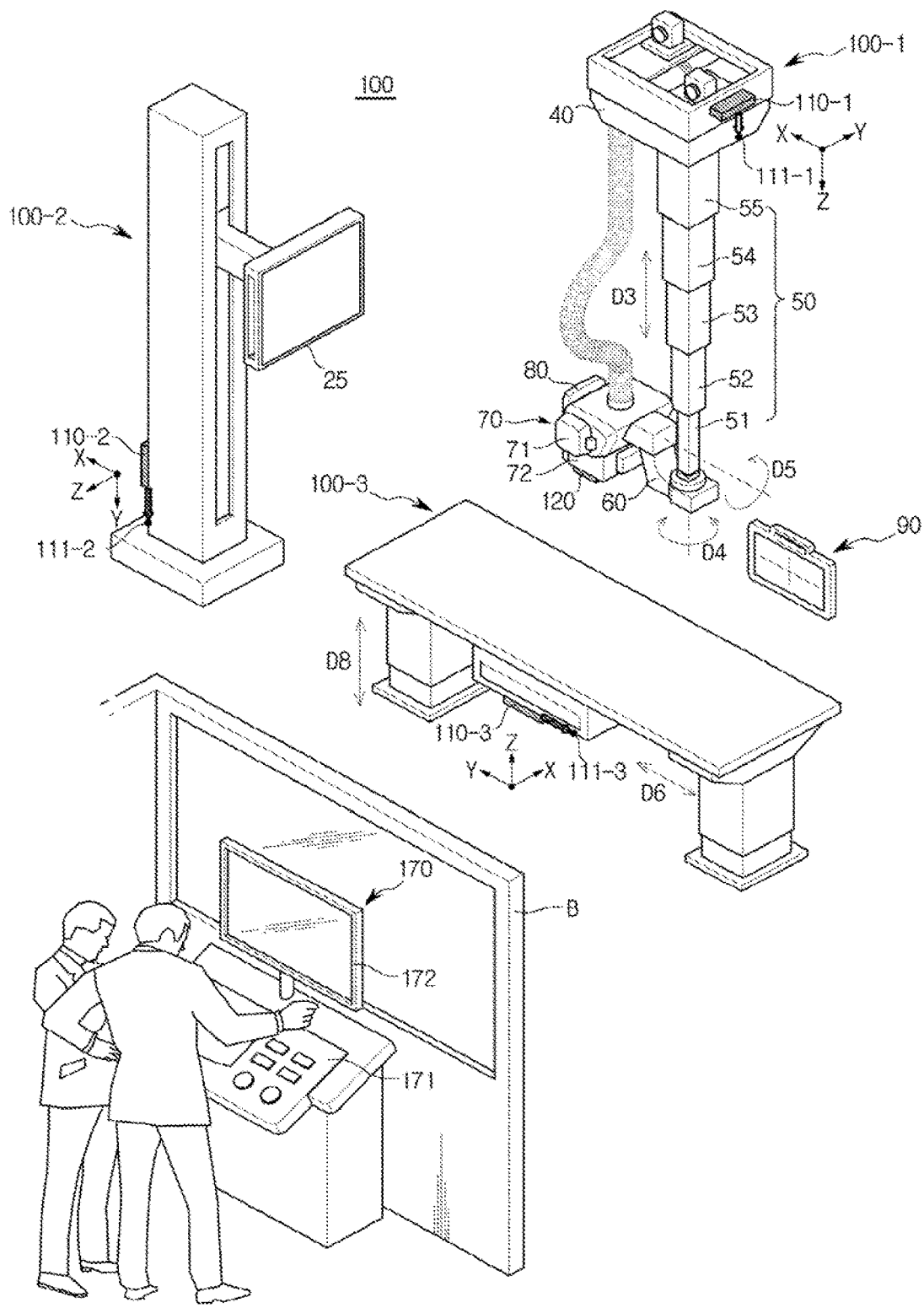

Referring to FIG. 9, the sensing portion 111 is be implemented using a magnetic sensor, and the magnetic sensor outputs different signals in accordance with positional relationships between first to third magnets 111-1, 111-2, and 111-3 mounted on the X-ray imaging apparatus 100 and the first to third processing boards 110-1, 110-2, and 110-3 respectively corresponding thereto.

For example, when a coordinate system of the magnetic sensor is formed by X-, Y-, and Z-axes as illustrated in FIG. 9, the magnetic sensor senses a magnetic force acting in one direction of the X-axis as a positive X-axial direction, a magnetic force acting in the opposite direction of the X-axis as a negative X-axial direction, a magnetic force acting in one direction of the Y-axis as a positive Y-axial direction, a magnetic force acting in the opposite direction of the Y-axis as a negative Y-axial direction, a magnetic force acting in one direction of the Z-axis as a positive Z-axial direction, and a magnetic force acting in the opposite direction of the Z-axis as a negative Z-axial direction.

When the first processing board 110-1 is mounted on the ceiling apparatus 100-1 such that a coordinate system of the first processing board 110-1 of the ceiling apparatus 100-1 is formed by the third direction D3, as the Z-axis, and the first direction D1, as the Y-axis, based on FIGS. 2 to 3 and 9, and the first magnet 111-1 is mounted vertically below the first processing board 110-1, the magnetic sensor senses the direction of the magnetic force as the positive Z-axial direction.

Also, when the second processing board 110-2 is mounted on the stand 100-2 such that a coordinate system of the second processing board 110-2 of the stand 100-2 is formed by the seventh direction D7, as the Y-axis, and the first direction D1, as the Z-axis, based on FIGS. 2 to 3 and 9, and the second magnet 111-2 is mounted vertically below the second processing board 110-2, the magnetic sensor senses the direction of the magnetic force as the positive Y-axial direction.

In addition, when the third processing board 110-3 is mounted on the table 100-3 such that a coordinate system of the third processing board 110-3 of the table 100-3 is formed by the eighth direction D8, as the Z-axis, and the first direction D1, as the X-axis, based on FIGS. 2 to 3 and 9, and the third magnet 111-3 is mounted on a right side of the third processing board 110-3, the magnetic sensor senses the direction of the magnetic force as the negative Y-axial direction.

In the same manner as described above, the magnetic sensor may also sense a direction having an output value greater than a predetermined threshold as the direction of the magnetic force.

Figure 10:
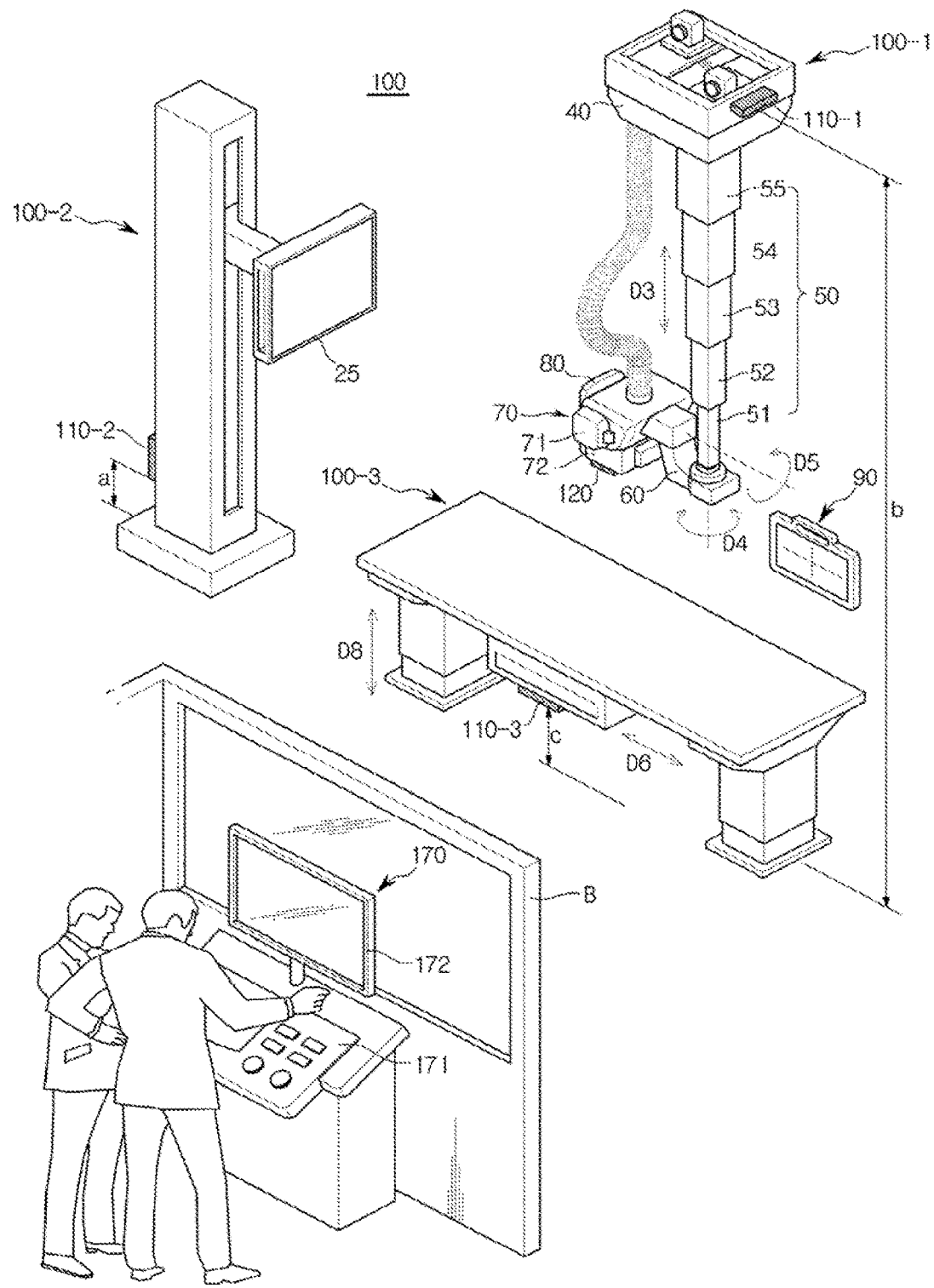

Meanwhile, referring to FIG. 10, the sensing portion 111 is implemented using a height sensor, and the height sensor outputs different signals in accordance with an altitude or height measured from the floor.

For example, when a height of the first processing board 110-1 mounted on the ceiling apparatus 100-1 measured from the floor is b, a height of the second processing board 110-2 mounted on the stand 100-2 measured from the floor is a, and a height of the third processing board 110-3 mounted on the table 100-3 measured from the floor is c as illustrated in FIG. 10, the height sensor senses the height of the first processing board 110-1 mounted on the ceiling apparatus 100-1 as b, the height of the second processing board 110-2 mounted on the stand 100-2 as a, and the height of the third processing board 110-3 mounted on the table 100-3 as c.

Figure 11:
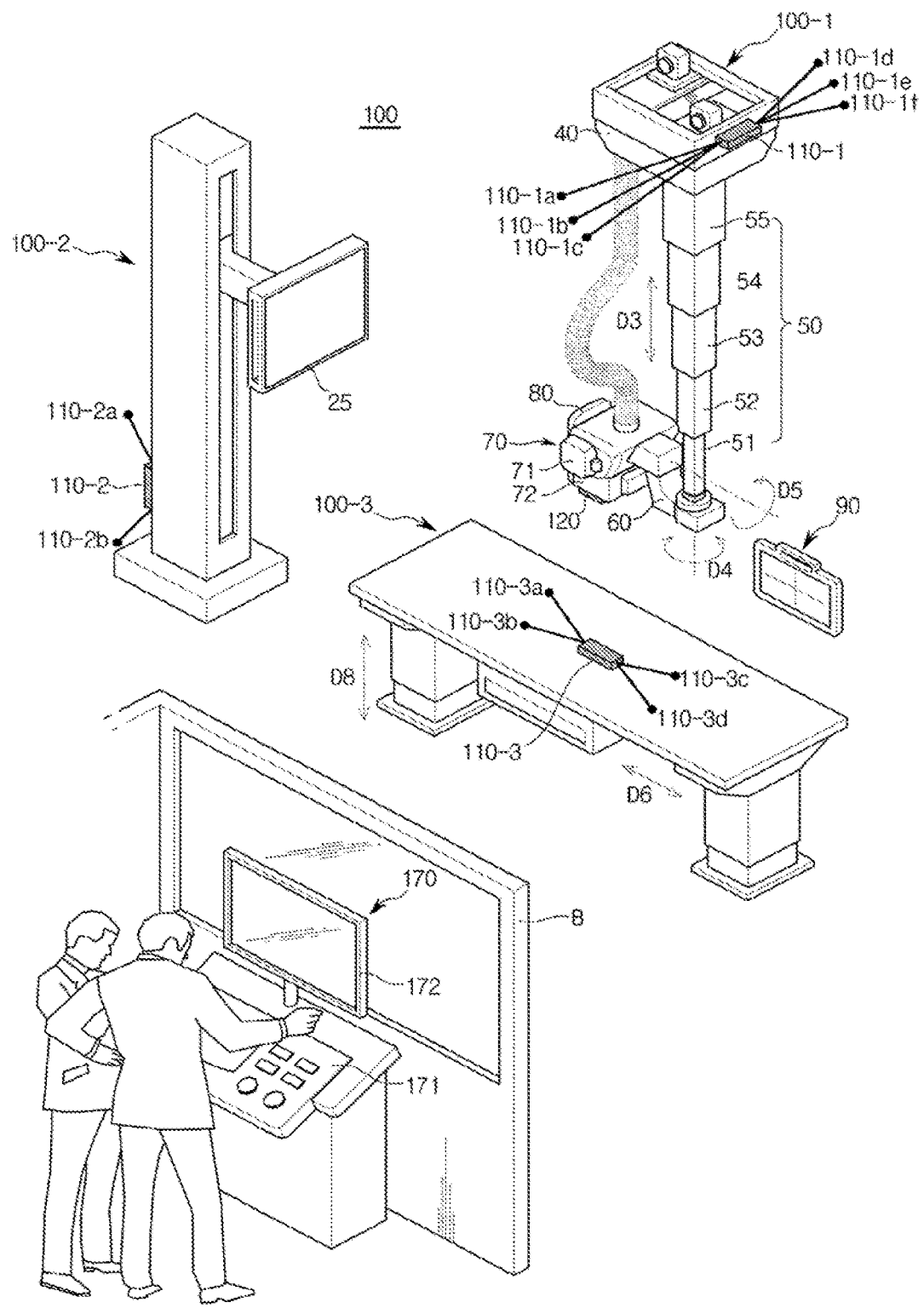

Referring to FIG. 11, the sensing portion 111 is implemented using a current sensor, and the current sensor outputs different signals in accordance with power consumptions of the first to third processing boards 110-1, 110-2, and 110-3.

For example, the first processing board 110-1 mounted on the ceiling apparatus 100-1 supplies current to the movable carriage 40, the post frame 50, the X-ray source 70, and the like to control various elements or devices installed in the ceiling apparatus 100-1 such as the movable carriage 40, the post frame 50, and the X-ray source 70. Hereinafter, at least one device installed in the ceiling apparatus 100-1 is referred to as first to sixth devices 110-1a, 110-1b, 110-1c, 110-1d, 110-1e, and 110-1f.

Also, the second processing board 110-2 mounted on the stand 100-2 supplies current to the second mounting portion 25, the X-ray detector 90, and the like to control various elements or devices installed in the stand 100-2 such as the second mounting portion 25 and the X-ray detector 90. Hereinafter, at least one device installed in the stand 100-2 is referred to as seventh to eighth devices 110-2a and 110-2b.

In addition, the third processing board 110-3 mounted on the table 100-3 supplied current to a table actuator, the X-ray detector 90, and the like to control various elements or devices installed in the table 100-3 such as the actuator and the X-ray detector 90. Hereinafter, at least one device installed in the table 100 is referred to as ninth to twelfth devices 110-3a, 110-3b, 110-3c, and 110-3d.

The current sensor of the first processing board 110-1 senses current supplied into the first to sixth devices 110-1a, 110-1b, 110-1c, 110-1d, 110-1e, and 110-1f from the first processing board 110-1. The current sensor of the second processing board 110-2 senses current supplied into the seventh to eighth devices 110-2a and 110-2b from the second processing board 110-2. The current sensor of the third processing board 110-3 senses current supplied into the ninth to twelfth devices 110-3a, 110-3b, 110-3c, and 110-3d from the third processing board 110-3.

Figure 12:
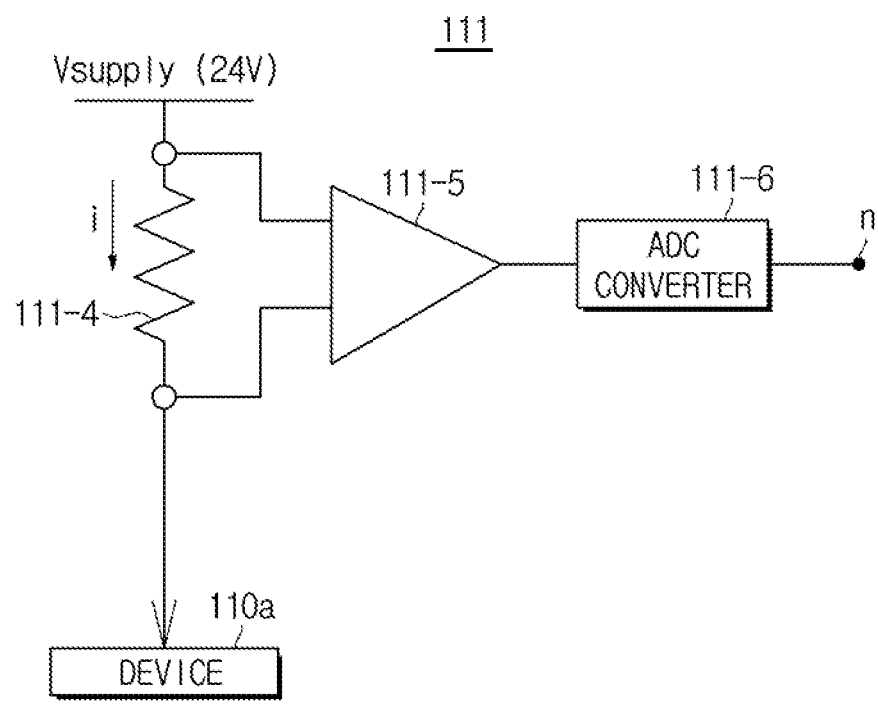

FIG. 12 is a circuit diagram of the sensing module 111 implemented using a current sensor.

Referring to FIG. 12, the current sensor includes a resistor 111-4, an amplifier 111-5, and an analog to digital converter (ADC) 111-6 to sense a current i supplied into a device 110a using a voltage Vsupply (e.g., 24 V) applied from the processing board 110. The amplifier 111-5 measures a voltage difference between both terminals of the resistor 111-4 connected to the device 110a, and the ADC converter 111-6 converts an output signal from the amplifier 111-5 into a digital signal, and outputs the converted signal to a node n. The current sensor senses the current i supplied into the device 110a based on the voltage difference between the terminals of the resistor 111-4 output from the node n and a resistance of the resistor 111-4. Meanwhile, the circuit diagram of the current sensor is not limited to that illustrated in FIG. 12, and may be implemented in various other forms used to sense current.

In addition, numbers of devices respectively connected to the first to third processing boards 110-1, 110-2, and 110-3 are not limited to those illustrated in FIG. 11.

As described above, the sensing portion 111 senses the mounted state of one of the first to third processing boards 110-1, 110-2, and 110-3 on the X-ray imaging apparatus 100. The mounted state may vary according to a sensor 111a (FIG. 14) included in the sensing portion 111 as described above.

Meanwhile, the sensing portion 111 may further include a switch 111b (FIG. 14) in addition to the sensor 111a, and the switch 111b may output different values in accordance with manual manipulation of the switch 111b by a user.

Figure 13:
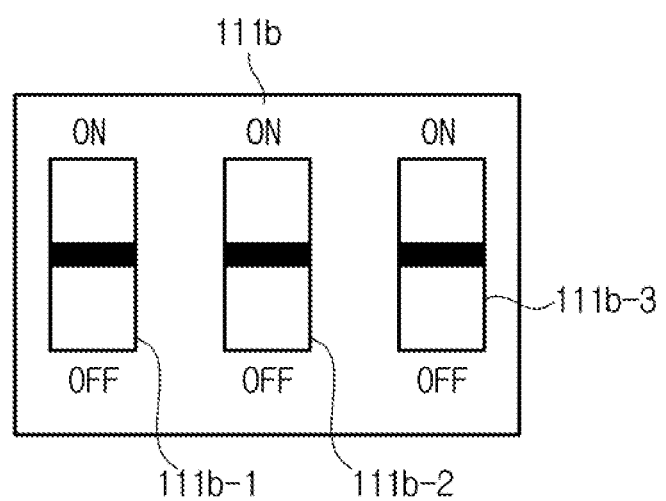
FIG. 13 is a diagram illustrating an appearance of a switch according to an exemplary embodiment.

FIG. 13 is a diagram illustrating an appearance of the switch 111b according to an exemplary embodiment.

Referring to FIG. 13, the switch 111b includes a first switch 111b-1, a second switch 111b-2, and a third switch 111b-3, and each of the first to third switches 111b-1, 111b-2, and 111b-3 may be turned on ON and turned off OFF according to manipulation thereof by a user. That is, each of the first to third switches 111b-1, 111b-2, and 111b-3 may output a binary number of 1 corresponding to turning on and a binary number of 0 corresponding to turning off.

For example, when the first switch 111b-1 is turned on, the second switch 111b-2 is turned off, and the third switch 111b-3 is turned off according to manipulation thereof by the user, the first to third switches 111b-1, 111b-2, and 111b-3 output 1, 0, and 0, respectively. When the first switch 111b-1 is turned off, the second switch 111b-2 is turned on, and the third switch 111b-3 is turned on according to manipulation thereof by the user, the first to third switches 111b-1, 111b-2, and 111b-3 output 0, 1, and 1, respectively.

As described above, the first to third processing boards 110-1, 110-2, and 110-3 may output different values according to the mounted state of the processing board 110 and the manual manipulation of the user by using the sensing portion 111.

Meanwhile, the processing board 110 may further include another element in addition to the sensing portion 111 to automatically set an ID.

Figure 14:
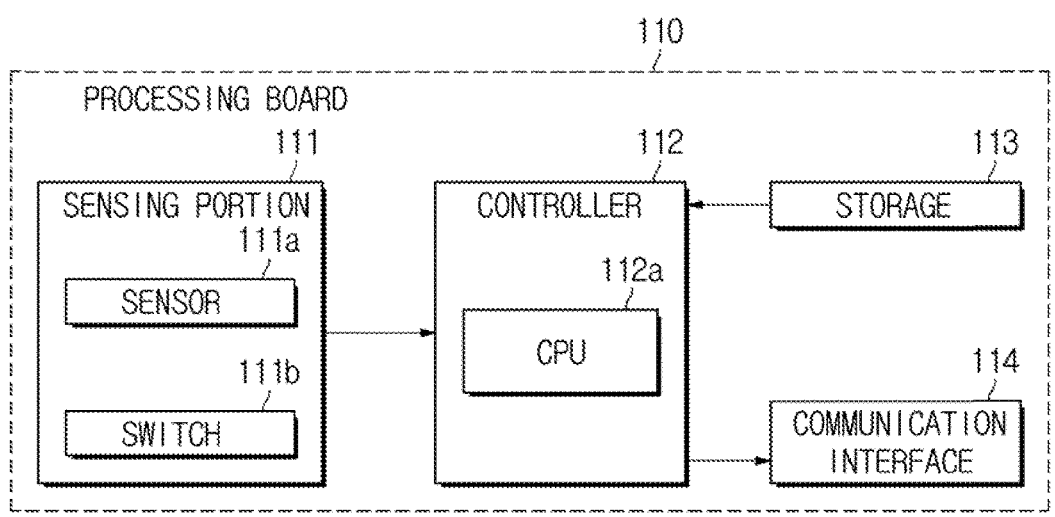
FIG. 14 is a control block diagram illustrating a processing board according to an exemplary embodiment.

FIG. 14 is a control block diagram illustrating the processing board 110 according to an exemplary embodiment.

Referring to FIG. 14, the processing board 110 includes the sensing portion 111 to sense a mounted state of the processing board 110, a controller 112 configured to set an ID of the processing board 110, a storage 113 in which an ID corresponding to an output value of the sensing portion 111 is pre-stored, and a communication interface 114 configured to transmit the set ID to the main processing board 84.

As described above, the sensing portion 111 includes the sensor 111a implemented using an accelerometer, a magnetic sensor, a height sensor, or a current sensor, and the switch 111b configured to receive manual manipulation of the switch 111b by a user.

The controller 112 includes the CPU 112a implemented using a microprocessor to control various elements of the X-ray imaging apparatus 100. The controller 112 sets the ID of the processing board 110 based on the output value of the sensing portion 111.

For example, when the sensing portion 111 is implemented using the accelerometer as illustrated in FIG. 6, and the accelerometer of the first processing board 110-1 outputs the positive Z-axial direction as the direction of gravity, the controller 112 searches for an ID corresponding to the positive Z-axial direction (e.g., 011) in the storage 113, and sets the found ID as an ID of the first processing board 110-1.

When the sensing portion 111 is implemented using the magnetic sensor as illustrated in FIG. 9, and the magnetic sensor of the first processing board 110-1 outputs the positive Z-axial direction as the direction of the magnetic force, the controller 112 searches for an ID corresponding to the positive Z-axial direction (e.g., 011) in the storage 113, and sets the found ID as an ID of the first processing board 110-1.

When the sensing portion 111 is implemented using the height sensor as illustrated in FIG. 10, and the height sensor of the first processing board 110-1 outputs b as the height from the floor, the controller 112 searches for an ID corresponding to the height b (e.g., 011) in the storage 113, and sets the found ID as an ID of the first processing board 110-1.

When the sensing portion 111 is implemented using the current sensor as illustrated in FIG. 11, and the current sensor of the first processing board 110-1 outputs a sum of currents supplied into the first to sixth devices 110-1a, 110-1b, 110-1c, 110-1d, 110-1e, and 110-1f as a power consumption, the controller 112 searches for an ID corresponding to the output sum of the currents (e.g., 011) in the storage 113, and sets the found ID as an ID of the first processing board 110-1.

The controller 112 may set IDs of the second and third processing boards 110-2 and 110-3 differently in accordance with the mounted states thereof in the same manner as the first processing board 110-1.

Meanwhile, the ID corresponding to the output value of the sensing portion 111 may be found not only in the storage 113 but also in the main processing board 84 via the communication interface 114. In this case, the controller 112 may set the ID of the processing board 110 by transmitting the output value of the sensing portion 111 to the main processing board 84 via the communication interface 114 and receiving an ID corresponding to the output value from the main processing board 84.

The controller 112 may also determine installation errors of the first processing board 110-1, the second processing board 110-2, and the third processing board 110-3 by comparing preset data of the first processing board 110-1 mounted on the ceiling apparatus 100-1, the second processing board 110-2 mounted on the stand 100-2, and the third processing board 110-3 mounted on the table 100-3, with output values of the sensing portion 111, respectively.

FIG. 15 is a table illustrating a method of determining an installation error of a processing board based on output values of a sensor implemented using an accelerometer according to an exemplary embodiment.

For example, it is assumed that the positive X-axial direction is preset for the first processing board 110-1 mounted on the ceiling apparatus 100-1, the negative X-axial direction is preset for the second processing board 110-2 of the stand 100-2, and the positive Y-axial direction is preset for the third processing board 110-3 of the table 100-3.

When the accelerometer of the first processing board 110-1 outputs the positive X-axial direction as the direction of gravity, the accelerometer of the second processing board 110-2 outputs the negative X-axial direction as the direction of gravity, and the accelerometer of the third processing board 110-3 outputs the positive Y-axial direction as the direction of gravity, the output values of the accelerometers are the same as the preset data. Thus, the controller 112 determines that the first to third processing boards 110-1, 110-2, and 110-3 are normally mounted on the X-ray imaging apparatus 100.

However, when the accelerometer of the first processing board 110-1 outputs the positive X-axial direction as the direction of gravity, the accelerometer of the second processing board 110-2 outputs the positive Z-axial direction as the direction of gravity, and the accelerometer of the third processing board 110-3 outputs the positive Y-axial direction as the direction of gravity, the output value of the accelerometer of the second processing board 110-2 is different from the preset data for the second processing board 110-2. Thus, the controller 112 determines that the second processing board 110-2 is abnormally mounted on the X-ray imaging apparatus 100. In this case, the controller 112 transmits data to the workstation 170 to inform the user of the installation error via the display 172 of the workstation 170.

In addition, when the sensing portion 111 further includes the switch 111b in addition to the sensor 111a, the controller 112 may determine the installation error of the processing board 110 based on output values of the sensor 111a and the switch 111b. That is, the controller 112 may determine the installation error of the processing board 110 by comparing the ID corresponding to the output value of the sensor 111a with the output values of the switch 111b.

For example, when the sensor 111a of the first processing board 110-1 implemented using the accelerometer outputs the negative X-axial direction as the direction of gravity and 010 is found as the ID corresponding to the negative X-axial direction, the output values of 1, 0, and 0 of the first to third switches 111b-1, 111b-2, and 111b-3 are different from the found ID (i.e., 010). Thus, the controller determines that the first processing board 110-1 is abnormally mounted. In this case, the controller 112 may also transmit data to the workstation 170 to inform the user of the installation error via the display 172 of the workstation 170.

In addition, the controller 112 may generate communication IDs for the first to third processing boards 110-1, 110-2, and 110-3 to access the main processing board 84 based on the set IDs.

FIG. 16 is a table illustrating controller area network (CAN) communication identifiers (IDs) corresponding to output values of a sensor implemented using an accelerometer according to an exemplary embodiment.

Referring to FIG. 16, the controller 112 may detect 0001 as an ID corresponding to the positive X-axial direction, and convert the found ID 0001 into an 11-bit CAN ID suitable for CAN communication (e.g., XXXXXXXXX01). Also, the controller 112 may detect 0100 as an ID corresponding to the negative X-axial direction, and convert the found ID 0100 into an 11-bit CAN ID suitable for CAN communication (e.g., XXXXXXXX100).

The controller 112 may also detect 0010 as an ID corresponding to the positive Y-axial direction, and convert the found ID 0010 into an 11-bit CAN ID suitable for CAN communication (e.g., XXXXXXXXX10). The controller 112 may also detect 0110 as an ID corresponding to the negative Y-axial direction, and convert the found ID 0110 into an 11-bit CAN ID suitable for CAN communication (e.g., XXXXXXXX110).

The controller 112 may also detect 0011 as an ID corresponding to the positive Z-axial direction, and convert the found ID 0011 into an 11-bit CAN ID suitable for CAN communication (e.g., XXXXXXXX11). The controller 112 may also detect 0101 as an ID corresponding to the negative Z-axial direction, and convert the found ID 0101 into an 11-bit CAN ID suitable for CAN communication (e.g., XXXXXXXX101).

Meanwhile, the CAN ID may have a variety of bit lengths such as 29 bits as well as 11 bits.

Although FIG. 16 shows CAN IDs as communication IDs for access to the main processing board 84, the controller 113 may also generate various other types of communication IDs in accordance with a communication network between the main processing board 84 and the first to third processing boards 110-1, 110-2, and 110-3.

Referring back to FIG. 14, the storage 113 stores IDs respectively corresponding to one or more output values of the sensing portion 111. For example, when the sensing portion 111 is implemented using the accelerometer or the magnetic sensor, the storage 113 may store 0001 as an ID corresponding to the positive X-axial direction, 0100 as an ID corresponding to the negative X-axial direction, 0010 as an ID corresponding to the positive Y-axial direction, 0110 as an ID corresponding to the negative Y-axial direction, 0011 as an ID corresponding to the positive Z-axial direction, and 0101 as an ID corresponding to the negative Z-axial direction.

Also, when the sensing portion 111 is implemented using the height sensor, the storage 113 may store 0001 as an ID corresponding to a height a, 0100 as an ID corresponding to a height b, 0010 as an ID corresponding to a height c, 0110 as an ID corresponding to a height d, 0011 as an ID corresponding to a height e, and 0101 as an ID corresponding to a height f.

When the sensing portion 111 is implemented using the current sensor, the storage 113 may store 0001 as an ID corresponding to a current i1, 0100 as an ID corresponding to a current i2, 0010 as an ID corresponding to a current i3, 0110 as an ID corresponding to a current i4, 0011 as an ID corresponding to a current i5, and 0101 as an ID corresponding to a current i6.

In addition, the storage 113 may pre-store expected output values of the sensing portions 111 of the first processing board 110-1 mounted on the ceiling apparatus 100-1, the second processing board 110-2 mounted on the stand 100-2, and the third processing board 110-3 mounted on the table 100-3. In this case, the controller 112 may determine installation errors of the first processing board 110-1, the second processing board 110-2, and the third processing board 110-3 by comparing the expected output values stored in the storage 113 with the output values of the sensing portions 111.

Besides, the storage 113 may store various types of data used to control the processing board 110. The storage 113 may include a Read Only-Memory (ROM) in which control programs to control each of the elements installed in the processing board 110, and a Random Access Memory (RAM) used as a storage corresponding to various operations performed by the controller 112.

The communication interface 114 transmits the ID of the processing board 110 set by the controller 112 to the main processing board 84. In this case, the communication interface 114 may transmits the ID of the processing board 110 in a format suitable for a communication network standard.

For example, when the first to third processing boards 110-1, 110-2, and 110-3 are connected to the main processing board 84 via a CAN communication network, the controller 112 converts the ID of the processing board 110 into the CAN ID, and the communication interface 114 transmits the generated CAN ID to the main processing board 84. For example, the CAN ID may have a bit length of 11 bits or 29 bits, without being limited thereto.

The communication interface 114 may also transmit a firmware update request signal to the main processing board 84, and receive a firmware update file therefrom. Firmware refer to a microprogram to control hardware components included in various elements of the processing board 110. The processing board 110 may improve performance of the hardware components included in the elements of the processing board 110 by receiving the firmware update file.

Meanwhile, when the processing board 110 is connected to the main processing board 84 via the CAN communication network, the communication interface 114 may be implemented using a CAN communication interface. However, the communication network is not limited thereto as described above, and the communication interface 114 may be implemented using a wired communication interface, a wireless communication interface, or a short-distance communication interface in accordance with the communication network.

Figure 17:
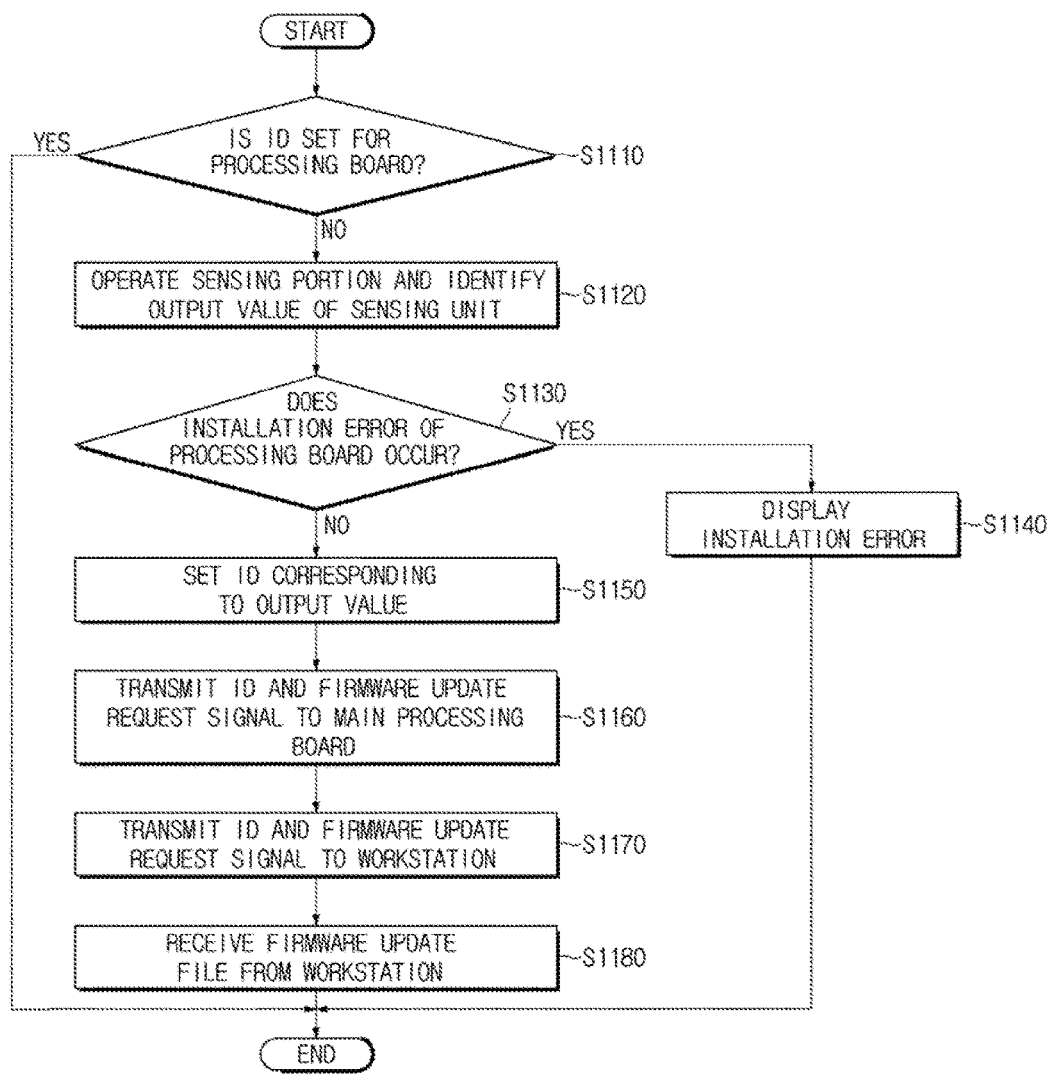
FIG. 17 is a flowchart illustrating a method of controlling an X-ray imaging apparatus according to an exemplary embodiment.

FIG. 17 is a flowchart illustrating a method of controlling an X-ray imaging apparatus according to an exemplary embodiment.

Hereinafter, the exemplary embodiment will be described on the assumption that at least one processing board is mounted on each of a ceiling apparatus, a stand, and a table of the X-ray imaging apparatus. A processing board mounted on the ceiling apparatus is referred to as a first processing board, a processing board mounted on the stand is referred to as a second processing board, and a processing board mounted on the table is referred to as a third processing board. In addition, a processing board mounted on a manipulation apparatus of the ceiling apparatus and controlling an overall operation of the first to third processing boards is referred to as a main processing board.

First, the main processing board determines whether an ID is set for a processing board among the first to third processing boards (S1110).

When an ID is not set for the processing board ("No" of S1110), the main processing board operates a sensing portion of the processing board for which the ID is not set, and the processing board for which the ID is not set identifies an output value of the sensing portion as a mounted state of the processing board (S1120).

For example, when the sensing portion is implemented using an accelerometer, the processing board for which the ID is not set may identify a direction of gravity as the mounted state of the processing board. Also, when the sensing portion is implemented using a magnetic sensor, the processing board for which the ID is not set may identify a relative position of a magnet previously mounted by a user as the mounted state of the processing board.

When the sensing portion is implemented using a height sensor, the processing board for which the ID is not set may identify a height of the processing board from a floor as the mounted state of the processing board. When the sensing portion is implemented using a current sensor, the processing board for which the ID is not set may identify a power consumption of the processing board as the mounted state of the processing board.

Then, the processing board for which the ID is not set determines whether an installation error of the processing board occurs (S1130). In detail, the processing board compares the identified output value of the sensing portion with pre-stored data.

When the output value of the sensing portion is different from the pre-stored data ("Yes" of S1130), the processing board for which the ID is not set transmits a control signal to a workstation to display a message informing the user of the occurrence of the installation error (S1140).

For example, when a "negative X-axial direction" is pre-stored as an expected output value of the first processing board mounted on the ceiling apparatus, and a "positive X-axial direction" is output as a direction of gravity from an accelerometer used as the sensing portion of the first processing board mounted on the ceiling apparatus, the expected output value is different from the output value of the accelerometer. Thus, the first processing board may transmit a control signal to the workstation to display a message informing that the first processing board is abnormally mounted (i.e., an installation error occurs).

For example, when a "negative Z-axial direction" is pre-stored as an expected output value of the first processing board mounted on the ceiling apparatus, and a "positive Y-axial direction" is output as a direction of a magnetic force from a magnetic sensor used as the sensing portion of the first processing board mounted on the ceiling apparatus, the expected output value is different from the output value of the magnetic sensor. Thus, the first processing board may transmit the control signal to the workstation to display the message informing that the first processing board is abnormally mounted (i.e., an installation error occurs).

For example, when a "height a" is pre-stored as an expected output value of the first processing board mounted on the ceiling apparatus, and a "height b" is output as a height of the first processing board from a height sensor used as the sensing portion of the first processing board mounted on the ceiling apparatus, the expected output value is different from the output value of the height sensor. Thus, the first processing board may transmit the control signal to the workstation to display the message informing that the first processing board is abnormally mounted (i.e., an installation error occurs).

For example, when a current of "200 mA" is pre-stored as an expected output value of the first processing board mounted on the ceiling apparatus, and a current of "0.5 mA" is output as a power consumption of the first processing board from a current sensor used as the sensing portion of the first processing board mounted on the ceiling apparatus, the expected output value is different from the output value of the current sensor. Thus, the first processing board may transmit the control signal to the workstation to display the message informing that the first processing board is abnormally mounted (i.e., an installation error occurs).

Meanwhile, the second and third processing boards may be mounted on various devices such as the stand and the table in addition to the ceiling apparatus, and expected values may vary according to mounted positions thereof.

When the output value of the sensing portion is the same as the pre-stored data ("No" of S1130), the processing board for which the ID is not set sets an ID corresponding to the output value of the sensing portion (S1150). The ID corresponding to the output value of the sensing portion may be found not only in the storage but also in the main processing board.

Then, the processing board for which the ID is set transmits the set ID and a firmware update request signal to the main processing board (S1160). In this case, the processing board for which the ID is set may convert the set ID into a format suitable for a communication network standard between the main processing board and the first to third processing boards. For example, when the first to third processing boards are connected to the main processing board via a CAN communication network, the ID of the processing board may be converted into a communication ID suitable for a CAN communication standard with a bit length of 11 bits or 29 bits, and the converted communication ID may be transmitted to the main processing board.

Then, the main processing board transmits the ID and firmware update request signal received from the processing board to a workstation (S1170). In this case, the main processing board may convert the received ID into a format suitable for a communication network standard between the main processing board and the workstation. For example, when the main processing board is connected to the workstation via a LAN communication network, the main processing board may convert the ID into a communication ID suitable for a LAN communication standard, and transmit the converted communication ID to the workstation.

Then, the workstation transmits a firmware update file corresponding to the received ID of the processing board to the processing board via the main processing board, and the processing board receives the firmware update file from the workstation via the main processing board (S1180). Similarly, for example, when the main processing board is connected to the workstation via the LAN communication network, the workstation may convert the firmware update file into data suitable for the LAN communication standard, and transmit the converted data to the main processing board. In addition, when the first to third processing boards are connected to the main processing board via the CAN communication network, the main processing board may convert the firmware update file into data suitable for the CAN communication standard, and transmit the converted data to the processing board.

In addition, the exemplary embodiments may also be implemented through computer-readable code and/or instructions on a medium, e.g., a non-transitory computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A processing board mounted on a medical diagnostic apparatus, the processing board comprising:
    a sensor configured to sense, as an output value, at least one selected from the group consisting of an installation position, an installation direction, and a power consumption of the processing board;
    a storage configured to store one or more identifier (ID) values for identifying the processing board in the medical diagnosis apparatus, along with one or more output values of the sensor, the one or more output values respectively corresponding to the one or more ID values;
    a communication interface; and
    a controller configured to:
        find, among the one or more ID values that are stored, an ID value corresponding to the output value that is sensed;
        set the ID value that is found, to identify the processing board in the medical diagnosis apparatus; and
        control the communication interface to transmit, to another processing board, the ID value that is set.

2. The processing board according to claim 1, wherein the communication interface comprises a controller area network (CAN) communication interface configured to transmit the ID value that is set, to the other processing board via a CAN communication network.

3. The processing board according to claim 1, wherein the sensor comprises at least one selected from the group consisting of an accelerometer, a magnetic sensor, a height sensor, and a current sensor.

4. The processing board according to claim 3, wherein the accelerometer is configured to sense a direction of gravity of the processing board with a strength greater than a threshold.

5. The processing board according to claim 1, further comprising a switch configured to output a switch value, based on a turn-on or turn-off input.

6. The processing board according to claim 1, wherein the medical diagnostic apparatus is one among an ultrasonic diagnostic apparatus, a magnetic resonance imaging apparatus, and a computed tomography apparatus.

7. The processing board according to claim 1, wherein the controller is further configured to control the communication interface to transmit, to the other processing board, a firmware update request of the processing board, along with the ID value that is set.

8. The processing board according to claim 7, wherein the communication interface is further configured to receive, from the other processing board, a firmware update file of the processing board, based on the firmware update request that is transmitted.

9. A medical diagnostic apparatus comprising:
    a processing board mounted on the medical diagnostic apparatus, the processing board being configured to:
        sense, as an output value, at least one selected from the group consisting of an installation position, an installation direction, and a power consumption of the processing board;
        store one or more identifier (ID) values for identifying the processing board in the medical diagnosis apparatus, along with one or more output values of a sensor, the one or more output values respectively corresponding to the one or more ID values;
        find, among the one or more ID values that are stored, an ID value corresponding to the output value that is sensed;
        set the ID value that is found, to identify the processing board in the medical diagnosis apparatus; and
    a main processing board configured to receive, from the processing board, the ID value that is set.

10. The medical diagnostic apparatus according to claim 9, wherein the processing board is further configured to:
    determine whether the output value that is sensed is different than an expected value of the at least one selected from the group consisting of the installation position, the installation direction, and the power consumption; and
    determine that an installation error of the processing board occurs based on the output value that is sensed being determined to be different than the expected value.

11. The medical diagnostic apparatus according to claim 9, further comprising a workstation configured to receive, from the main processing board, the ID value that is set.

12. The medical diagnostic apparatus according to claim 9, further comprising:
    an X-ray source configured to generate X-rays, and emit the X-rays to an object;
    a ceiling apparatus configured to move the X-ray source toward the object;
    an X-ray detector configured to detect X-rays having passed through the object; and
    a table and a stand on which the X-ray detector is mounted.

13. The medical diagnostic apparatus according to claim 12, wherein the processing board comprises a first processing board, a second processing board, and a third processing board,
    the first processing board is mounted on the ceiling apparatus,
    the second processing board is mounted on the stand, and
    the third processing board is mounted on the table.

14. The medical diagnostic apparatus according to claim 9, wherein the medical diagnostic apparatus is one among an ultrasonic diagnostic apparatus, a magnetic resonance imaging apparatus, and a computed tomography apparatus.

15. The medical diagnostic apparatus according to claim 9, wherein the main processing board controls the processing board, using the ID value that is received.

16. The medical diagnostic apparatus according to claim 9, wherein the storage is further configured to store a predetermined table comprising the one or more ID values being mapped to the one or more output values of the sensor, and
    the controller is further configured to find, among the predetermined table that is stored, the ID value mapped to the output value that is sensed.

17. A method of controlling a medical diagnostic apparatus, the method comprising:
    sensing, as an output value, at least one selected from the group consisting of an installation position, an installation direction, and a power consumption of a processing board mounted on the medical diagnostic apparatus;

storing one or more identifier (ID) values for identifying the processing board in the medical diagnosis apparatus, along with one or more output values of a sensor, the one or more output values respectively corresponding to the one or more ID values;

finding, among the one or more ID values that are stored, an ID value corresponding to the output value that is sensed;

setting the ID value that is found, to identify the processing board in the medical diagnosis apparatus; and transmitting, to another processing board, the ID value that is set.

18. The method according to claim 17, wherein the sensing comprises sensing a direction of gravity of the processing board with a strength greater than a threshold.

19. The method according to claim 17, further comprising transmitting, to the other processing board, a firmware update request of the processing board, along with the ID value that is set.

20. The method according to claim 19, further comprising receiving, from the other processing board, a firmware update file of the processing board, based on the firmware update request that is transmitted.

21. A processing board mounted on a medical diagnostic apparatus, the processing board comprising:

a sensor configured to sense an output value of at least one among a direction of gravity, a direction of a magnetic force, a height from a floor, and a current of the processing board;

a storage configured to store one or more identifier (II)) values for identifying the processing board in the medical diagnosis apparatus, along with one or more output values of the sensor, the one or more output values respectively corresponding to the one or more ID values;

a communication interface; and a controller configured to:

determine whether an installation error of the processing board occurs, based on the output value that is sensed;

based on the installation error being determined to not occur, find, among the one or more ID values that are stored, an ID value corresponding to the output value that is sensed;

set the ID value that is found, to identify the processing board in the medical diagnosis apparatus; and control the communication interface to transmit, to another processing board, the ID value that is set.

22. The processing board according to claim 21, wherein the controller is further configured to:

determine whether the output value that is sensed is different than an expected value of the at least one among the direction of gravity, the direction of the magnetic force, the height from the floor, and the current of the processing board; and determine that the installation error occurs, based on the output value that is sensed being determined to be different than the expected value.

23. The processing board according to claim 21, further comprising a switch configured to output a switch value, based on a turn-on or turn-off input, wherein the controller is further configured to:

determine whether the ID value that is set is different than the switch value that is output; and determine that the installation error occurs, based on the ID value being determined to be different than the switch value that is output.

\* \* \* \* \*